(12) United States Patent
Tameishi et al.

(10) Patent No.: US 6,575,947 B1
(45) Date of Patent: Jun. 10, 2003

(54) INDIVIDUALLY PACKAGED ABSORBENT ARTICLE

(75) Inventors: Kazuaki Tameishi, Hyogo (JP); Nami Terada, Kobe (JP)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/787,446

(22) PCT Filed: Oct. 5, 1998

(86) PCT No.: PCT/US98/21023

§ 371 (c)(1), (2), (4) Date: Mar. 19, 2001

(87) PCT Pub. No.: WO00/19953

PCT Pub. Date: Apr. 13, 2000

(51) Int. Cl.[7] .................................................. A61F 13/15
(52) U.S. Cl. .............................. 604/385.01; 604/385.02; 604/385.4
(58) Field of Search ................................. 604/317–402, 604/385.04, 385.02

(56) References Cited

U.S. PATENT DOCUMENTS 5,413,568 A 5/1995 Roach et al.
6,074,376 A 6/2000 Mills

FOREIGN PATENT DOCUMENTS

GB 2 306 428 A 5/1997
WO WO 98/42285 10/1998

Primary Examiner—Jeanette Chapman
(74) Attorney, Agent, or Firm—Matthew P. Fitzpatrick; Roddy M. Bullock; Ingrid N. Hickman

(57) ABSTRACT

An individually packaged absorbent article is disclosed. The individually packaged absorbent article comprises an absorbent article and a wrapper. The absorbent article extends in a longitudinal direction and includes a main body portion having a pair of longitudinal side edges, a pair of end edges, a garment surface, and a body surface. The absorbent article includes a pair of flaps joined to the main body portion and extending laterally outward beyond the longitudinal side edges of the main body portion. The garment surface of each of the flaps has a flap fastener. The flaps are folded over the body surface of the main body portion to expose the flap fasteners. The wrapper for the absorbent article has a main wrapper sheet. The body surface of the main body portion is disposed to face the main wrapper sheet. The flap fastener of the flap is releasably affixed to the main wrapper sheet. The main body portion and the wrapper are folded as a unit at least about one transverse axis such that the garment surface is oriented inwardly with respect to the folded unit.

9 Claims, 20 Drawing Sheets

INDIVIDUALLY PACKAGED ABSORBENT ARTICLE

FIELD

This invention relates to an individually packaged absorbent article.

BACKGROUND

Absorbent articles which are used to absorb body exudates, such as disposable diapers, adult incontinence products or sanitary napkins are well known. Such absorbent articles typically have a body surface which may include a liquid permeable topsheet, a garment surface which may include a liquid impermeable backsheet, and an absorbent therebetween. When the absorbent article is used, the body surface of the absorbent article is placed facing the wearer's body and the garment surface is placed against the wearer's undergarment. The body surface of the absorbent article should be kept hygienic prior to use of the absorbent article because the body surface directly touches the wearer's body. Typically, an absorbent article such as a sanitary napkin is individually wrapped by a wrapper to protect the absorbent article from contamination. Such individually packaged absorbent articles are disclosed in, for example, JP Utility Model Laid-open publication 95/39820 published on Jul. 18, 1995, JP Utility Model Laid-open publication 94/75446 published on Oct. 25, 1994, and JP Patent Laid-open publication 91/176376 published on Jul. 31, 1991. In certain know designs, an absorbent article such as a sanitary napkin is folded into three portions such that the body surface of the sanitary napkin is oriented inwardly to the folded sanitary napkin and the garment surface is wrapped by a wrapper. The body surface is protected from the wearer touching before the sanitary napkin is unfolded for application to the wearer's undergarment. However, the wearer opens and removes the wrapper from the sanitary napkin and unfolds the sanitary napkin when applying the sanitary napkin to a wearer's undergarment. This causes body surface contamination because the wearer tends to apply the sanitary napkin by touching the body surface and/or by pushing the body surface of the sanitary napkin toward the undergarment to secure the main fastener provided on the garment surface to the undergarment. Thus, there is no convenient means to protect the body surface of the sanitary napkin while the wearer applies the sanitary napkin to the undergarment. Such known sanitary napkins may also have flaps extending laterally outward from the main body portion of the sanitary napkin. In a configuration where the sanitary napkin is packaged, the flaps are folded on the topsheet. Although the flaps folded onto the topsheet can provide protection for the body surface during the application of the sanitary napkin, the flaps do not cover the whole area of the body surface of the sanitary napkin which may touch the wearer's body, i.e., portions of the body surface are still left umprotected.

Attempts to protect the body surface of the sanitary napkin during application of the sanitary napkin to the undergarment have been made. For example, JP Patent Laid-open publication 96/56989 published on Mar. 5, 1996 discloses an absorbent article such as a sanitary napkin having a surface cover sheet covering the body surface of the main body portion of the sanitary napkin. A part of the surface cover sheet is temporarily joined to the body surface by a hot melt adhesive. When the sanitary napkin is applied to the undergarment, the wearer does not touch the body surface of the sanitary napkin because the body surface is protected by the surface cover sheet. Although this sanitary napkin protects the body surface from contamination during the application process of the sanitary napkin, the sanitary napkin requires a joint means, such as the hot melt adhesive, to affix the surface cover sheet to the body surface of the sanitary napkin. Even after the surface cover sheet is removed from the body surface, the hot melt adhesive may remain on the body surface. If the sanitary napkin with the body surface having the hot melt adhesive is used, it is possible to cause a skin problem or the wearer feels stickiness while wearing the sanitary napkin. Additionally, processing steps are necessary for applying the adhesive between the body surface and the surface cover sheet.

Based on the foregoing, there is a need for an absorbent article individually packaged by a wrapper having a main wrapper sheet; wherein the body surface of the absorbent article remains protected from, e.g., the wearer's hands during unwrapping and application. None of the existing art provides all of the advantages and benefits of the present invention.

SUMMARY

The present invention provides an individually packaged absorbent article. The individually packaged absorbent article comprises an absorbent article and a wrapper. The absorbent article extends in a longitudinal direction and includes a main body portion having a pair of longitudinal side edges, a pair of end edges, a garment surface, and a body surface. The absorbent article includes a pair of flaps joined to the main body portion and extending laterally outward.beyond the longitudinal side edges of the main body portion. The garment surface of each of the flaps has a flap fastener. The flaps are folded over the body surface of the main body portion to expose the flap fasteners. The wrapper for the absorbent article has a main wrapper sheet. The body surface of the main body portion is disposed to face the main wrapper sheet. The flap fastener of the flap is releasably affixed to the main wrapper sheet. The main body portion and the wrapper are folded as a unit at least about one transverse axis such that the garment surface is oriented inwardly with respect to the folded unit.

The present invention further provides an individually packaged absorbent article. The individually packaged absorbent article comprises an absorbent article and a wrapper. The absorbent article extends in a longitudinal direction and includes a main body portion having a pair of longitudinal side edges, a pair of end edges, a garment surface, and a body surface. The absorbent article includes a pair of first flaps joined to the main body portion and extending laterally outward beyond the longitudinal side edges of the main body portion, and a pair of second flaps joined to the main body portion apart from the first flaps in the longitudinal direction and extending laterally outward beyond the longitudinal side edges of the main body portion. The garment surface of each of the first and second flaps has a first flap fastener and a second flap fastener respectively. The first and second flaps are folded over the body surface of the main body portion to expose the first and second flap fasteners. The wrapper for the absorbent article has a main wrapper sheet. The body surface of the main body portion is disposed to face the main wrapper sheet. The first flap fastener and the second flap fastener are releasably affixed to the main wrapper sheet. The main body portion and the wrapper are folded as a unit at least about one transverse axis such that the garment surface is oriented inwardly with respect to the folded unit.

BRIEF DESCRIPTION OF THE DRAWINGS

While the specification concludes with claims which particularly point out and distinctly claim the invention, it is believed the present invention will be better understood from the following description of preferred embodiments taken in conjunction with the accompanying drawings, in which like reference numerals identify identical elements and wherein:

DETAILED DESCRIPTION OF THE INVENTION

All cited references are incorporated herein by reference in their entireties, Citation of any reference is not an admission regarding any determination as to its availability as prior art to the claimed invention.

"Comprising" means that other steps and other elements which do not affect the end result can be added. This term encompasses the terms "consisting of" and "consisting essentially of".

Individually wrapped absorbent articles such as sanitary napkins are useful to protect the absorbent article from contamination. In order to protect a body surface of an absorbent article from contamination during application of the absorbent article to the undergarment, a wrapper to protect the body surface may be provided. However, if the wrapper is releasably affixed to the body surface by applying adhesive between the wrapper and the body surface, it is possible to cause a skin problem and/or the wearer feels stickiness while wearing the absorbent article because the adhesive may remain on the body surface even after removal of the wrapper. Additional processing steps are necessary for applying the adhesive between the body surface and the wrapper. The present invention answers the need for an individually wrapped absorbent article whose body surface remains protected from, e.g., the wearer's hands during unwrapping and application of the absorbent article. Additionally, the present invention avoids the need for certain adhesives (e.g., on the body surface of the absorbent article) which may otherwise cause discomfort (e.g., felling of strechiness, and/or cause skin problems) to the wearer. Additionally, the subject invention eliminates the need for certain processing steps otherwise required by previously known individually wrapped absorbent articles. These and other features of the present invention are discussed in more detail below.

Figure 1:
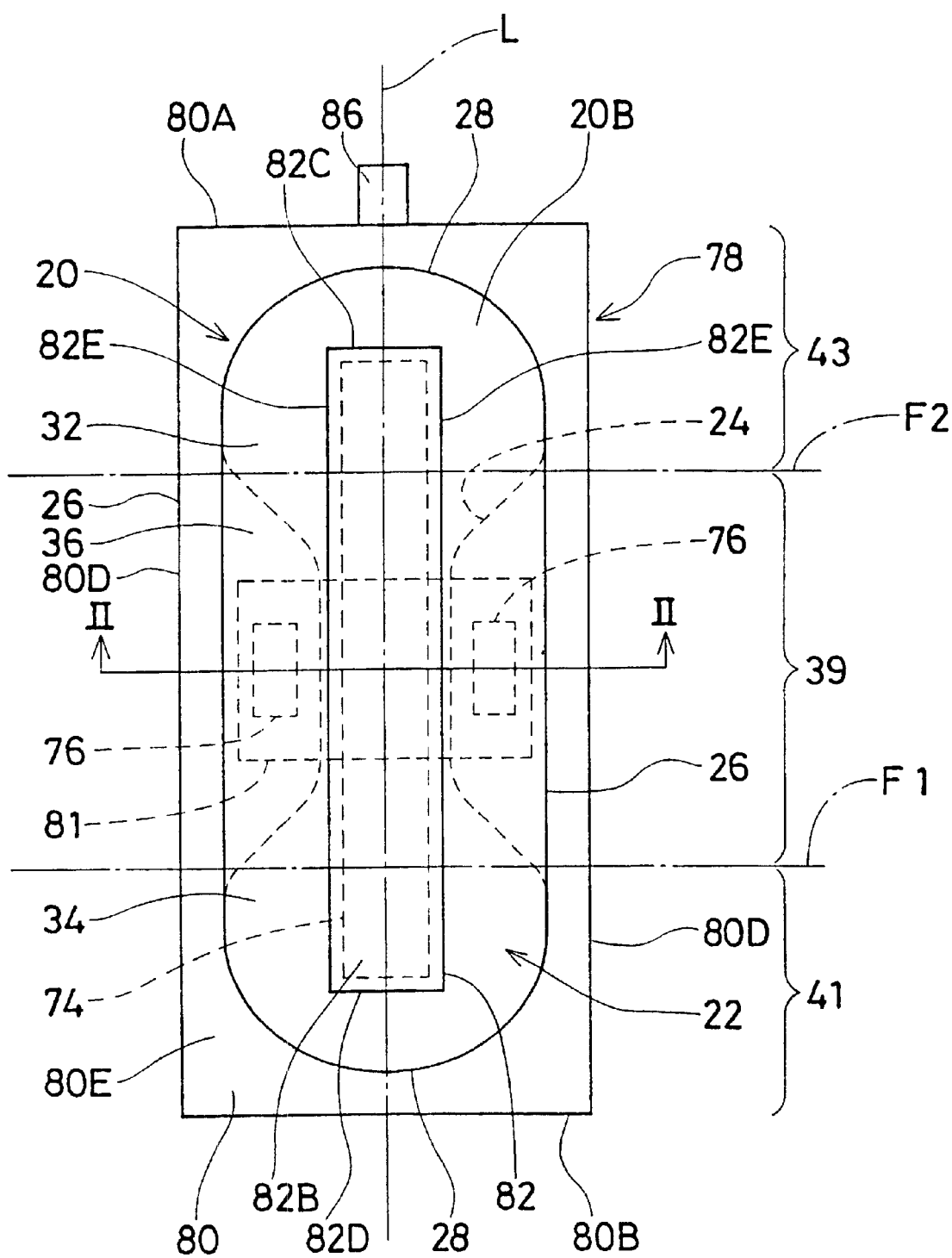
FIG. 1 is a top plan view of a preferred embodiment of the wrapper of the present invention in an opened position with a preferred sanitary napkin disposed thereon.
Figure 2:
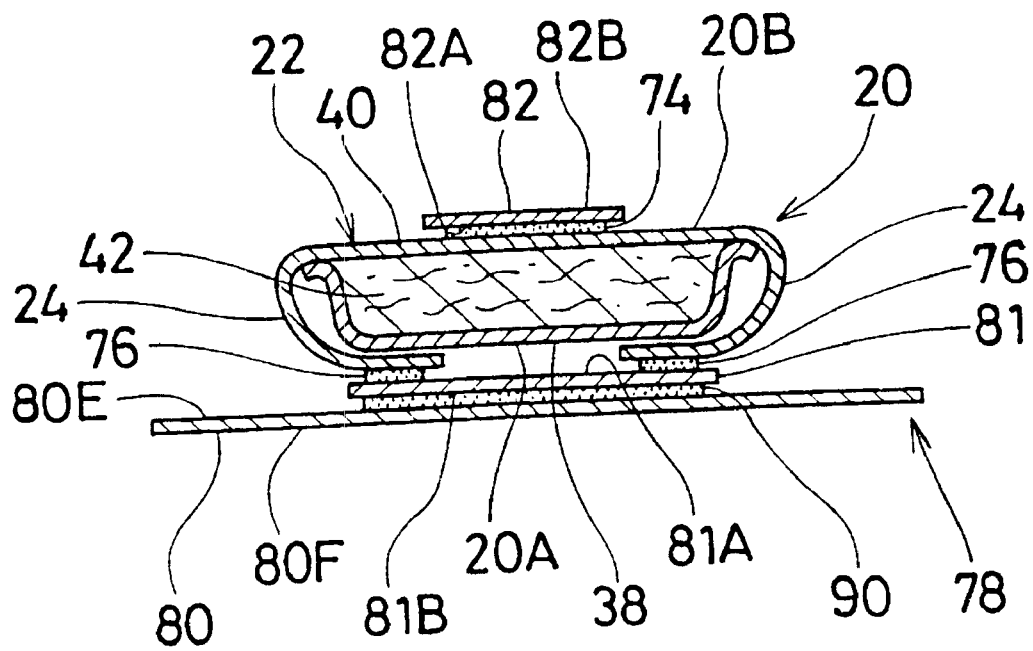
FIG. 2 is a cross-sectional view of the wrapper and the sanitary napkin taken along the line II—II of FIG. 1.

Referring now to the drawings, the present invention is described in a preferred but non-limiting embodiment. As shown in FIGS. 1 and 2, the present invention includes a wrapper 78 for a disposable absorbent article, particularly a sanitary napkin 20.

Figure 3:
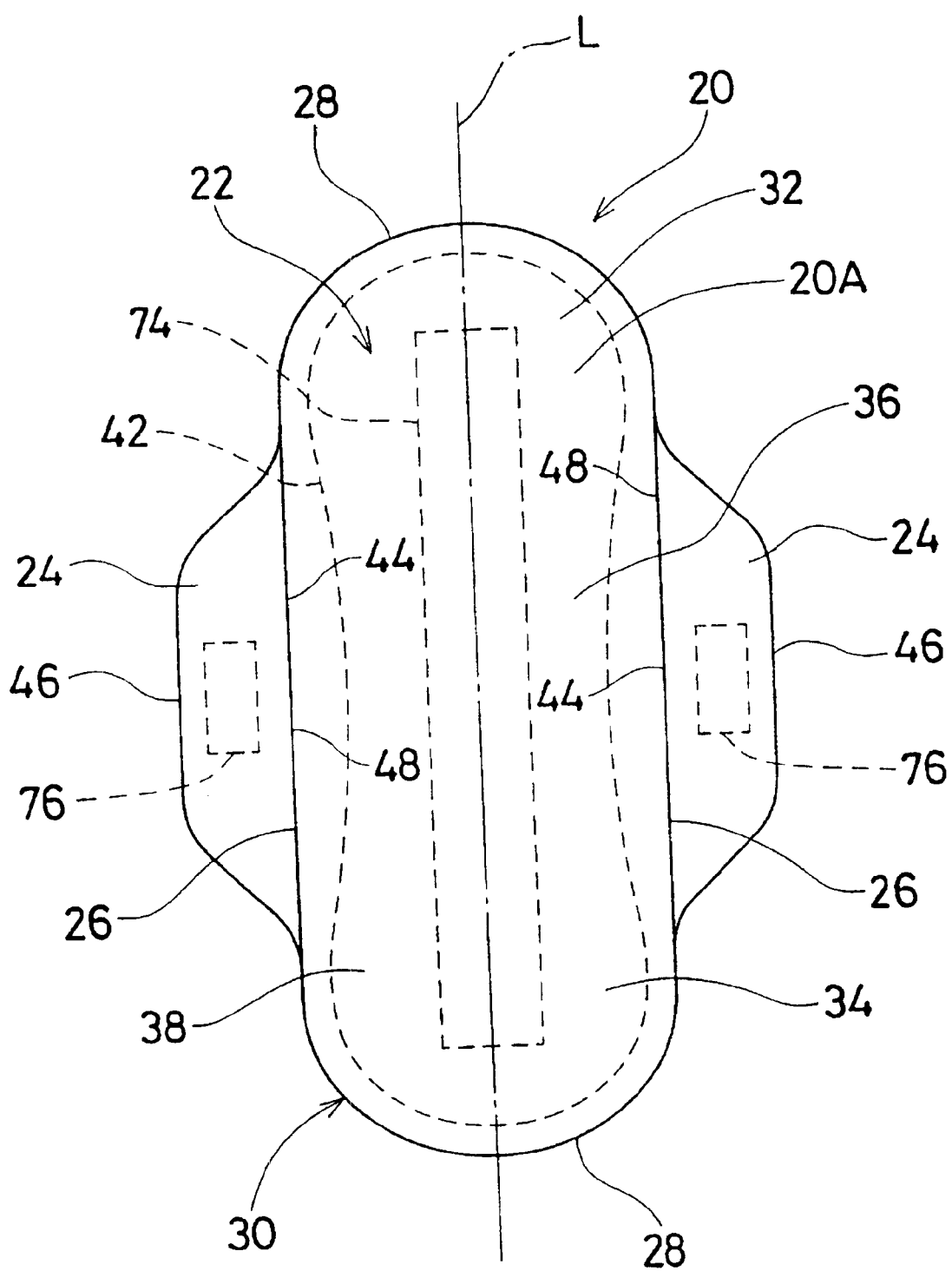
FIG. 3 is a top plan view of the sanitary napkin shown in FIG. 1 with the flaps outstretched.

The sanitary napkin 20 is used to collect vaginal discharges, such as menses, and prevent soiling of the wearer's clothing by such discharges. As shown in FIGS. 1, 2, and 3, the sanitary napkin 20 basically includes a main body portion 22 and a pair of flaps 24 (first flaps) which will be folded to wrap the edge of the wearer's undergarment when in use. The main body portion 22 of the sanitary napkin 20 may have a main body fastener, such as a pressure sensitive adhesive fastener thereon for fastening the main body portion 22 in the wearer's undergarment. The first flaps 24 preferably each have flap fasteners thereon, such as a pressure sensitive adhesive fastener, for releasably affixing the first flaps 24 of the sanitary napkin 20 in a configuration folded around the edges of the crotch of the wearer's undergarment. The wrapper 78 serves to cover and protect the flap fasteners and the body surface of the sanitary napkin 20, and is folded around the sanitary napkin 20 to provide an individual package for the sanitary napkin 20. The sanitary napkin 20 (and the main body portion 22 thereof) has two surfaces, a liquid pervious body-contacting surface or "body surface" 20A that is intended to be worn adjacent to the body of the wearer, and a liquid impervious garment surface 20B. The sanitary napkin 20 is shown in FIG. 3 as viewed from its body surface 20A. The sanitary napkin 20 (with the other elements, such as the wrapper 78) is shown in FIG. 1 as viewed from its garment surface 20B. The sanitary napkin 20 has two centerlines, a principal longitudinal centerline L and a principal transverse centerline (not shown in FIGS). Herein "longitudinal" refers to a line, axis or direction in the plane of the sanitary napkin 20 that is generally aligned with (e.g. approximately parallel to) a vertical plane which bisects a standing wearer into left and right body halves when the sanitary napkin 20 is worn. Herein "transverse" "lateral" or "width", are interchangeable, and refer to a line, axis or direction which lies within the plane of the sanitary napkin 20 that is generally perpendicular to the longitudinal direction. FIG. 3 shows the main body portion 22 and the first flaps 24 of the sanitary napkin 20. The main body portion 22 has two spaced apart longitudinal side edges 26, two spaced apart transverse or end edges (or "ends") 28, which together form the periphery 30 of the main body portion 22. The main body portion 22 also has three sections including a central section (first section) 36, one end section (second section) 34 and the other end section (third section) 32. The first section 36 is disposed between the second section 34 and the third section 32. The second section 34 and the third section 32 extend outwardly in the longitudinal direction from the edges of the central section 36 of the main body portion 22. When the sanitary napkin 20 is individually packaged, the main body portion 22 and the wrapper 78 are folded as a unit into three regions including a first region 39, a second region 41, and a third region 43 divided by two fold axes F1 and F2 (refer to FIG. 1). The first section 36, the second section 34 and the third section 32 of the main body portion 22 generally extend in the first region 39, the second region 41 and the third region 43, respectively.

The main body portion 22 of the sanitary napkin 20 can be of any thickness, including relatively thick, intermediate thickness, relatively thin, or even very thin (or "ultra thin"). An "ultra-thin" sanitary napkin 20 as described in U.S. Pat. Nos. 4,950,264 and 5,009,653 issued to Osborn on Aug. 21, 1990 and Aug. 23, 1991 respectively preferably has a caliper of less than about 3 millimeters. The embodiment of the sanitary napkin 20 shown in the drawings is intended to be an example of a sanitary napkin of an intermediate thickness. The main body portion 22 of the sanitary napkin 20 may also be relatively flexible, so that it is comfortable for the wearer. It should be understood that the sanitary napkin shown is merely one embodiment, and that the wrapper of the present invention is not limited to use with absorbent articles of the type or having the specific configurations shown in the drawings.

FIG. 2 shows the individual components of the main body portion 22 of the sanitary napkin 20. The main body portion 22 of the sanitary napkin 20 preferably has at least three primary components. These include a liquid pervious topsheet 38, a liquid impervious backsheet 40, and an absorbent core 42 positioned between the topsheet 38 and the backsheet 40. The topsheet, the backsheet, and the absorbent core may be assembled in a variety of configurations known in the art (including layered or "sandwich" configurations and wrapped or "tube" configurations). Suitable materials for the components of the main body portion 22, and some of the various configurations in which such components can be assembled are described generally in, e.g., U.S. Pat. No. 4,321,924, entitled "Bordered Disposable Absorbent Article" issued to Ahr on Mar. 30, 1982; U.S. Pat. No. 4,425,130, entitled "Compound Sanitary Napkin" issued to DesMarais on Jan. 10, 1984; U.S. Pat. No. 4,950,264, entitled "Thin, Flexible Sanitary Napkin" issued to Osborn on Aug. 21, 1990; U.S. Pat. No. 5,308,346, entitled "Elasticized Sanitary Napkin" issued to Sneller, et al. on May 3, 1994; and U.S. Pat. No. 5,389,094, entitled "Absorbent Article Having Flaps and Zones of Differential Extensibility" issued to Lavash, et al. on Feb. 14, 1995. The main body portion 22 of the sanitary napkin 20 may also be formed by one or more extensible components such as those sanitary napkins, and the like described in, e.g., U.S. patent application Ser. Nos. 07/915,133 and 07/915,284, both filed Jul. 23, 1992, in the name of Osborn, et al. (PCT Publication Nos. WO 93/01785 and 93/01786, both published Feb. 4, 1993).

FIG. 2 shows a preferred embodiment of the sanitary napkin 20 assembled in a sandwich construction in which the topsheet 38 and the backsheet 40 have length and width dimensions generally larger than those.of the absorbent core 42. The topsheet 38 and the backsheet 40 extend beyond the edges of the absorbent core 42 to form portions: of the periphery 30. The topsheet 38 is preferably joined to the body-facing side of the absorbent core 42 and the backsheet 40 is preferably joined to the garment-facing side of the absorbent core 42. The topsheet 38 and backsheet 40 can be joined to the absorbent core 42 in any suitable manner known in the art for this purpose, such as by an open pattern of adhesives. The portions of the topsheet 38 and backsheet 40 that extend beyond the edges of the absorbent core 42 are preferably also joined to each other. These portions of the topsheet 38 and backsheet 40 can also be joined in any suitable manner known in the art. Preferably, in the embodiment shown, these portions of the topsheet 38 and backsheet 40 are joined using adhesives over substantially the entire portions that extend beyond the edges of the absorbent core 42, and a crimp seal around the periphery 30 of the main body portion 22 where the topsheet 38 and backsheet 40 are densified by the application of pressure or heat and pressure.

The sanitary napkin 20 shown in FIG. 3, as discussed above, also has a pair of first flaps 24 that are joined to the main body portion 22. The first flaps 24 extend laterally outward beyond the longitudinal side edges 26 of the main body portion 22 from their proximal edges 44 to their distal edges (or "free ends") 46. The first flaps 24 extend laterally outward from at least a part of the first section 36 of the main body portion 22 and majority of the first flaps 24 extends in the first region 39 divided by the fold axes F1 and F2 (refer to FIG. 1).

The first flaps 24 can be joined to the main body portion 22 in any suitable manner. Herein "joined" encompasses configurations in which an element is directly secured to another element by affixing the element directly to the other element; configurations in which the element is indirectly secured to the other element by affixing the element to intermediate member(s) which in turn are affixed to the other element; and configurations in which one element is integral with another element, i.e., one element is essentially part of the other element. Preferably, in the embodiment shown in FIG. 3, the first flaps 24 are integral with the main body portion 22 (that is, the flaps 24 are formed by integral extensions of the backsheet 40; alternatively, the flaps 24 may be formed by integral extensions of the topsheet 38 and the backsheet 40 which are coextensive). In other alternative embodiments, the flaps 24 can be formed by one or more separate components that are joined to the garment-facing side of the main body portion 22. Preferably, in such a case, the flaps 24 each are formed by a separate component that is joined to the garment-facing side of the main body portion 22. In such alternative embodiments, the flaps 24 are preferably otherwise unattached to the garment-facing side of the main body portion 22 of the sanitary napkin 20 between the points where they are attached to the main body portion 22 and the longitudinal side edges 26 of the main body portion 22. The flaps 24 in these latter embodiments can be joined to the garment-facing side of the main body portion 22 by any suitable attachment mechanism. Suitable attachment mechanisms include, but are not limited to adhesives, and the like. The places or regions on the sanitary napkin 20 where the flaps 24 are joined to (or extend from) the main body portion 22, are referred to herein as "junctures". These regions will typically be longitudinally-oriented (or "longitudinal") junctures, such as lines of juncture 48. These regions can be any of various curved or straight lines, but they are not limited to lines. Thus, the junctures may include flanges, strips, intermittent lines, and the like.

The first flaps 24 may be of any configuration desired. For example, the first flaps 24 are provided with zones of extensibility24 (not shown in FIGS.) in the front edge and the back edge of each flap. The zones of extensibility relieve stresses which are created in the first flaps 24 by the folding of the first flaps 24 around the crotch of the wearer's undergarment. The zones of extensibility thereby help eliminate bunching of the first flaps 24 caused by said stresses. The zones of extensibility may be formed by pre-corrugated or "ring rolled" regions of the first flaps 24 in which the corrugations define ridges and valleys that are oriented at an angle to the principal longitudinal centerline L. Suitable structures for providing the flaps 24 with zones of extensibility are described in greater detail in, e.g., U.S. Pat. No. 5,389,094 issued to Lavash, et al. and in commonly assigned copending U.S. patent application Ser. No. 08/380,769, entitled "Absorbent Article Having Flaps With Gathered Portions" filed in the name of Sue A. Mills, et al. on Jan. 30, 1995.

Figure 4:
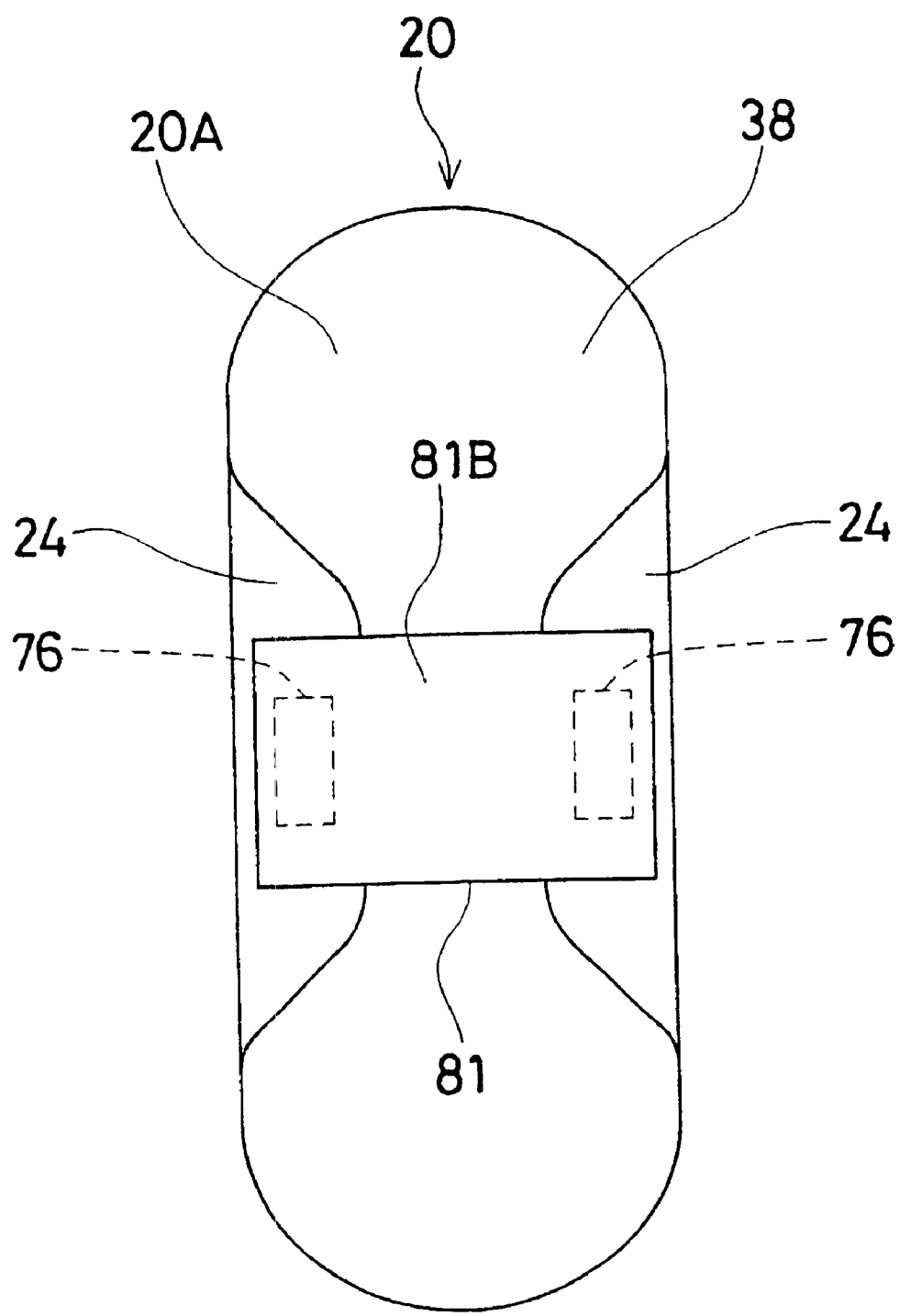
FIG. 4 is a top plan view of the sanitary napkin shown in FIG. 1 with the flaps folded over the topsheet and covered by the flap fastener cover.

The sanitary napkin 20 preferably also has fasteners for securing the sanitary napkin 20 in place in a wearer's undergarment. FIGS. 3 and 4 show a preferred arrangement of fasteners which includes a main body fastener, such as a main body adhesive 74, and flap fasteners, such as first flap adhesives 76. The fasteners used with the sanitary napkin 20 are not limited to adhesive fasteners. Any suitable type of fastener known in the art can be used for this purpose. For example, the sanitary napkin 20 could be secured in place in a wearer's undergarment by mechanical fasteners, such as VELCRO®, or by a combination of adhesive and mechanical fasteners. For simplicity, however, the fasteners will be described in terms of adhesive fasteners and these fasteners are preferably pressure sensitive adhesive fasteners. Suitable pressure sensitive adhesive fasteners are described in greater detail in, e.g., U.S. Pat. No. 4,917,697 issued to Osborn, et al. on Apr. 17, 1990.

The main body adhesive 74 and the first flap adhesives 76 can be provided in any suitable configuration. In the preferred embodiment shown in FIGS. 1 and 3, the main body adhesive 74 is provided in the form of one longitudinally oriented strip of adhesive that is centered about the principal longitudinal centerline L. The main body adhesive 74 may be provided in the form of two or more longitudinally oriented strips of adhesive which are disposed parallel to each other. Alternatively, the main body adhesive 74 may be provided in the form of two or more generally rectangular patches of adhesive which are disposed in the longitudinal direction at a distance. The first flap adhesives 76 are provided in the form of a generally rectangular patch of adhesive on each first flap 24. The main body adhesive 74 provides an adhesive attachment means for securing the main body portion 22 of the sanitary napkin 20 against the crotch portion of a panty. The first flap adhesives 76 are used to assist in maintaining the first flaps 24 in position after they are wrapped around the edges of the crotch portion of the panty. The flaps can be maintained in position by attaching the flaps 24 to the undergarment, or to the opposing flap.

FIGS. 1 and 2 show one preferred version of the wrapper 78. The wrapper 78 may be formed by a single element or may be formed by several elements. These elements can be formed by integral portions of a single member or article, or they can be formed by separate components joined to a member or article. The elements constituting the wrapper 78 include: a main wrapper sheet 80; and a flap fastener cover 81, such as a separate flap adhesive cover sheet or a release coating disposed on one, side of the main wrapper sheet 80; optionally may include a main fastener cover 82. The main wrapper sheet 80 is the portion of the wrapper 78 which will be folded around the sanitary napkin 20 to provide an individual package for the sanitary napkin 20. The main wrapper sheet 80 preferably covers the side of the body surface 20A of the sanitary napkin 20 and is releasably affixed to the sanitary napkin 20 as described hereinafter. The main wrapper sheet 80 has two surfaces, inner surface 80E and outer surface 80F. The inner surface 80E is the surface facing the sanitary napkin 20. The main wrapper sheet 80 preferably has dimensions that are slightly larger than those of the main body portion 22 of the sanitary napkin 20. Preferably, as shown in FIG. 1, the main wrapper sheet 80 has longitudinal side portions 80D which extend beyond the longitudinal side edges 26 of the main body portion 22 of the sanitary napkin 20. The main wrapper sheet 80 preferably also has a first end portion 80A and a second end portion 80B which extend beyond the end edges 28 of the main body portion 22. It is recognized, however, that satisfactory protection of sanitary napkin 20 may be afforded by a wrapper which is not larger than the main body portion 22 of the sanitary napkin 20. The main wrapper sheet 80 can be made from any suitable material. The main wrapper sheet 80 is preferably manufactured from a thin flexible material which is liquid impermeable so that the wrapper 78 will be suitable for wrapping and disposing of a used sanitary napkin 20. For example, polyethylene films have been found to work well. The main wrapper sheet 80 may be formed by opaque material, a semi-transparent material, or a transparent material. An opaque main wrapper sheet 80 offers the advantage of discreteness when used to rewrap a used/soiled sanitary for disposal. However, a semi-transparent or a transparent main wrapper sheet 80 facilitates visual placement of the sanitary napkin onto the undergarment.

The flap fastener cover (or "flap adhesive cover") 81 covers and protects the first flap adhesives 76 in a packaged configuration of the sanitary napkin 20 by the wrapper 78. It also maintains the first flaps 24 in position folded over the topsheet 38. FIG. 4 shows one example of the flap adhesive cover 81 formed by a separate flap adhesive cover sheet before the flap adhesive cover 81 is joined to the main wrapper sheet 80. The flap adhesive cover 81 may be formed by a thin sheet-like element such as a paper or a plastic film. If a separate release paper is used, it can be formed by any suitable material known in the art for this purpose, such as coated papers. Suitable release papers are described in, e.g., U.S. Pat. No. 4,917,697 issued to Osborn, Apr. 17 1990. Such a release paper 81 can be laminated to the inner surface 80E of the main wrapper sheet 80 as shown in FIG. 2 before or after the flap adhesive cover 81 is releasably affixed to the first flap adhesives 76. The flap adhesive cover 81 has two faces, one of which is a non-stick face (or releasable face) 81A which is- capable of releasable attachment with the flap fasteners, and an opposite face or side 81B. As shown in FIG. 2, the non-stick face 81A is disposed to face the first flap adhesives 76 such that it will be able to releasably adhere to the first flap adhesive 76. When the flap fasteners are formed.by adhesive fasteners, the non-stick face 81A can be provided by attaching a separate release paper or element to the flap adhesive cover 81 which is treated with a non-stick material, or by treating all or a portion of the flap adhesive cover 81 with a non-stick coating, such as by silicone coating a portion of the flap adhesive cover 81. Alternatively, if the flap fasteners 76 are formed by mechanical fasteners, such as VELCRO® fasteners, the non-stick face may be provided by a nonwoven material capable of releasably engaging the mechanical fastening material. The opposite side 81B faces away from the first flap adhesives 76 as shown in FIGS. 2 and 4. The opposite side 81B of the flap adhesive cover 81 need not have, and preferably does not have, a release coating thereon. The opposite side 81B is joined to the inner surface 80E of the main wrapper sheet 80 by any suitable means such as adhesive layer 90 as shown in FIG. 2. As the main wrapper sheet 80 is removed from the sanitary napkin 20, the flap adhesive cover 81 is removed from the first flap adhesives 76 of the sanitary napkin 20 while remaining on the main wrapper sheet 80.

Figure 5:
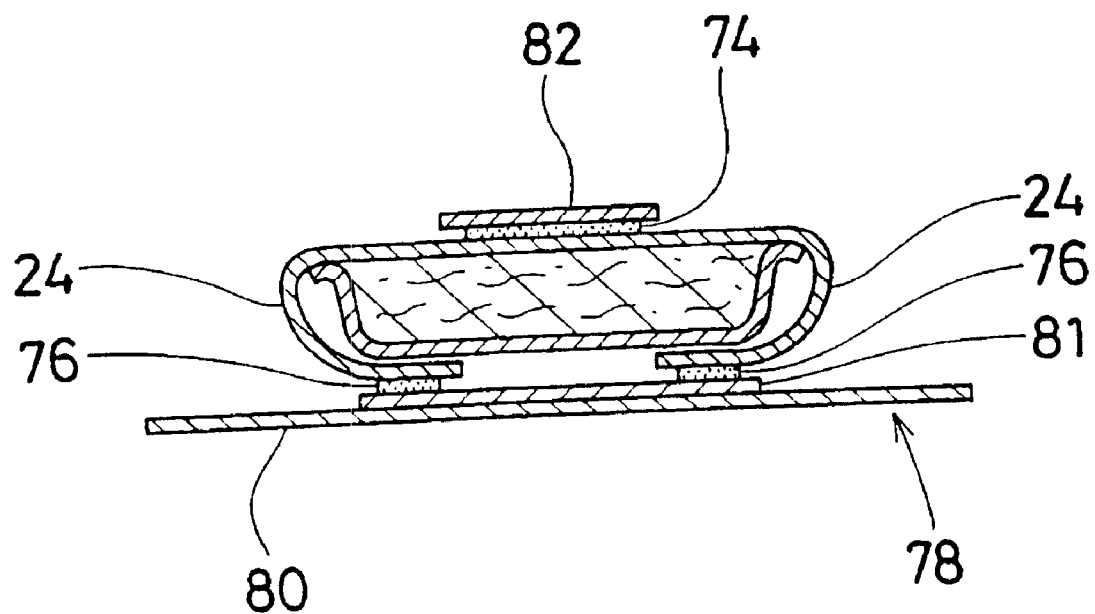
FIG. 5 is a cross-sectional view of an alternate embodiment of the wrapper and the sanitary napkin.

Alternatively, as shown in FIG. 5, the flap adhesive cover 81 may be provided on the main wrapper sheet 80 as a release coating. The first flap adhesives 76 may be releasably affixed to the release coating 81. If a release coating is used, the coating can be applied directly to the inner surface 80E of the main wrapper sheet 80. Such a coating can be formed by any material known in the art for this purpose, with silicone coatings being preferred. If a coating is used, the coating 81 may be provided by coating only that zone of the main wrapper sheet 80 which will substantially contact the first flap adhesives 76. Alternatively, the entire inner surface 80E of the main wrapper sheet 80 may be coated Coating the entire inner surface of a wrapper is disclosed in, e.g., U.S. Pat. No. 5,181,610 entitled "Flexible Container with Nonstick Interior" which issued to Quick et al. on Jan, 26, 1993.

The main fastener cover (or "main adhesive cover") 82 may be provided to cover and protect the main body adhesive 74 if it is provided. The main adhesive cover 82 may also be formed by a thin sheet-like element such as a paper or a plastic film and have two faces, one of which is a non-stick face (or releasable face) 82A which is capable of releasable attachment with the main fastener, and an opposite face or side 82B. The main adhesive cover 82 also has longitudinal side portions 82E, a first end portion 82C located proximate to the first end portion 80A of the main wrapper sheet 80, and a second end portion 82D located proximate to the second end portion 80B of the main wrapper sheet 80. In the embodiment shown in FIG. 1, the first end portion 82C is located in the third region 43 and the second end portion 82D is located in the second region 41. Preferably, as shown in FIG. 2, the non-stick face 82A of the main adhesive cover 82 faces the main body adhesive 74 such that it will be able to releasably adhere to the main body adhesive 74. The non-stick surface 82A may be formed by the same material or element as the non-stick face 81A of the flap adhesive cover 81. The opposite side 82B may, or may not have a release coating thereon. The flap adhesive cover 81 and the main adhesive cover 82 can be of any suitable size and shape, though the figures depict a flap adhesive cover 81 and a main adhesive cover 82 which are only of sufficient width and length to cover and protect the first flap adhesives 76 and the main body adhesive 74. The wrapper 78 preferably also may include an optional package fastener 86 for retaining the package formed by folding the wrapper and sanitary napkin in its folded configuration. The package fastener 86 is preferably both releasably attachable to the package and resealable. The package fastener 86 may be formed by any releasably attachable and resealable fastener known in the art, such as spots or patches of adhesive, tapes, and mechanical fasteners. A package fastener with a pressure sensitive adhesive located thereon has been found to work well. The package fastener 86 can be disposed at any suitable location on the wrapper 78. In the embodiment shown in FIG. 1, the package fastener 86 is preferably positioned at opposing first end portion 80A of the main wrapper sheet 80.

Figure 6:
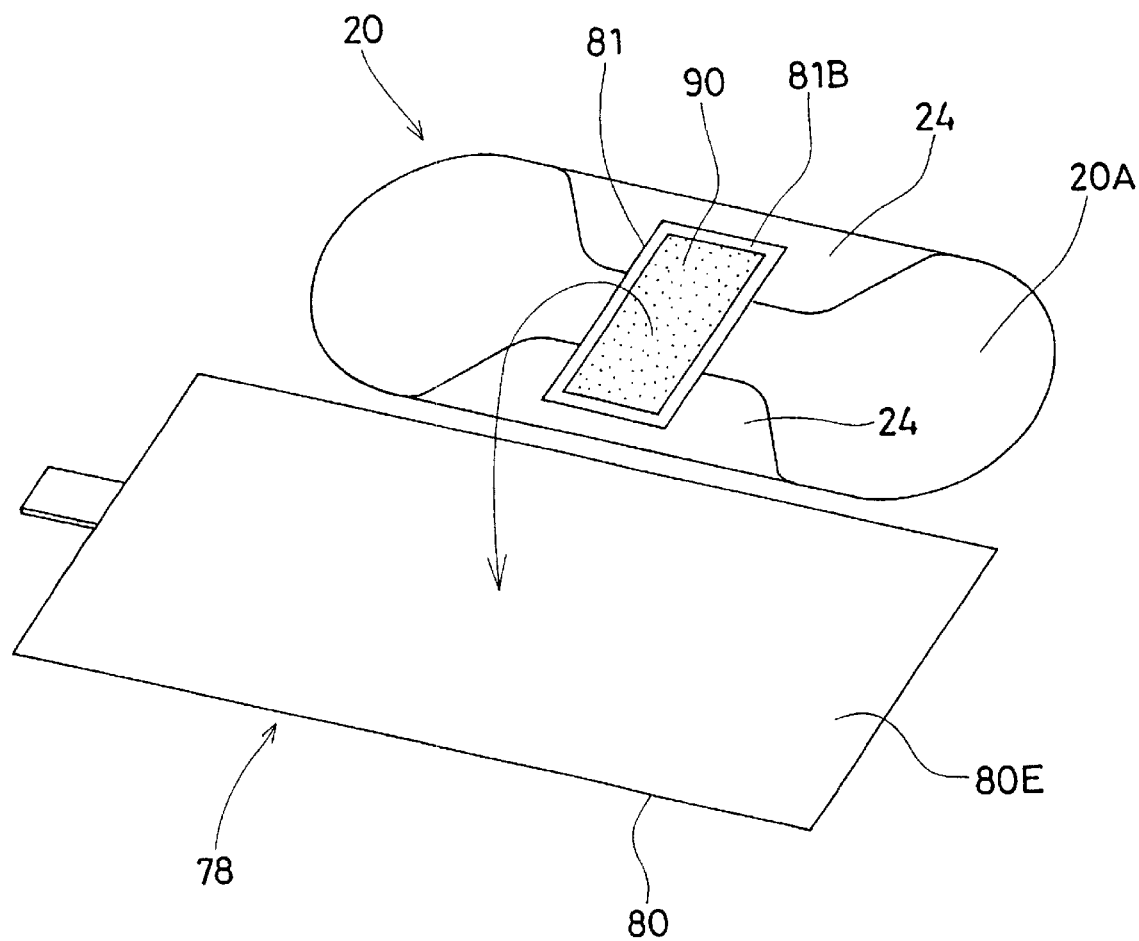
FIG. 6 is a first schematical perspective view showing a packaging process of the sanitary napkin by the wrapper.
Figure 7:
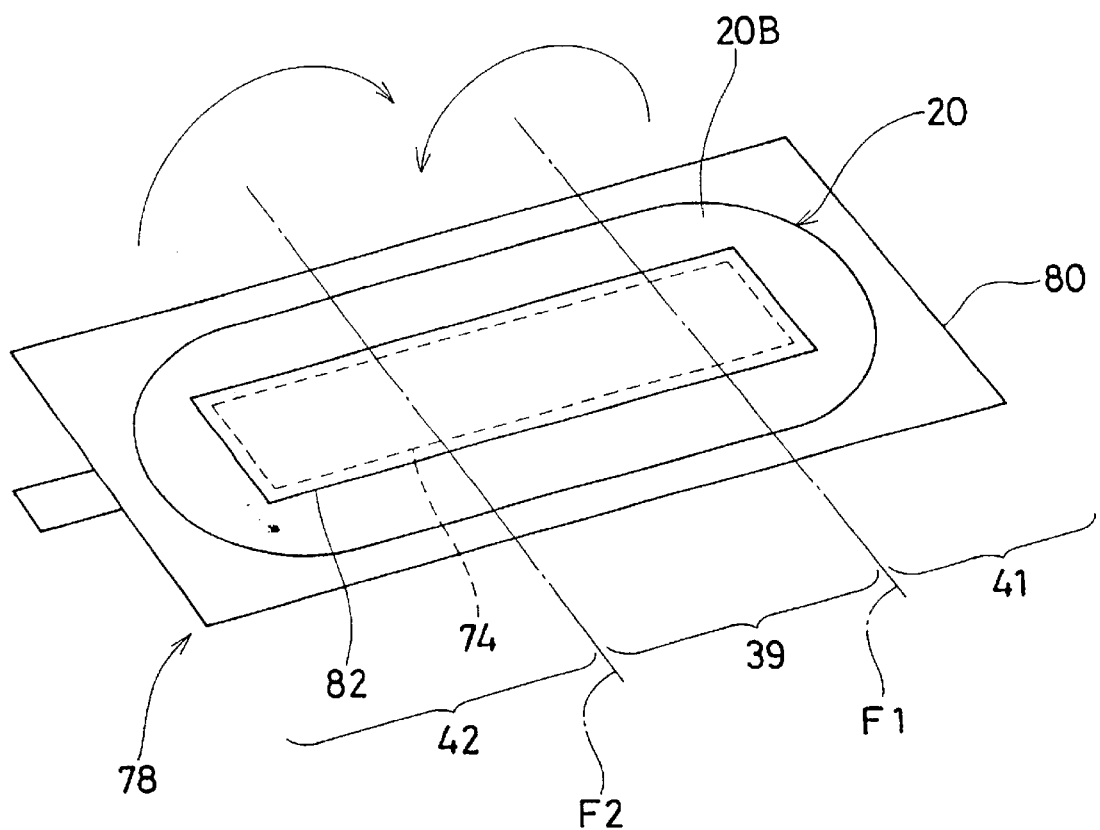
FIG. 7 is a second schematical perspective view showing a packaging process of the sanitary napkin by the wrapper.
Figure 8:
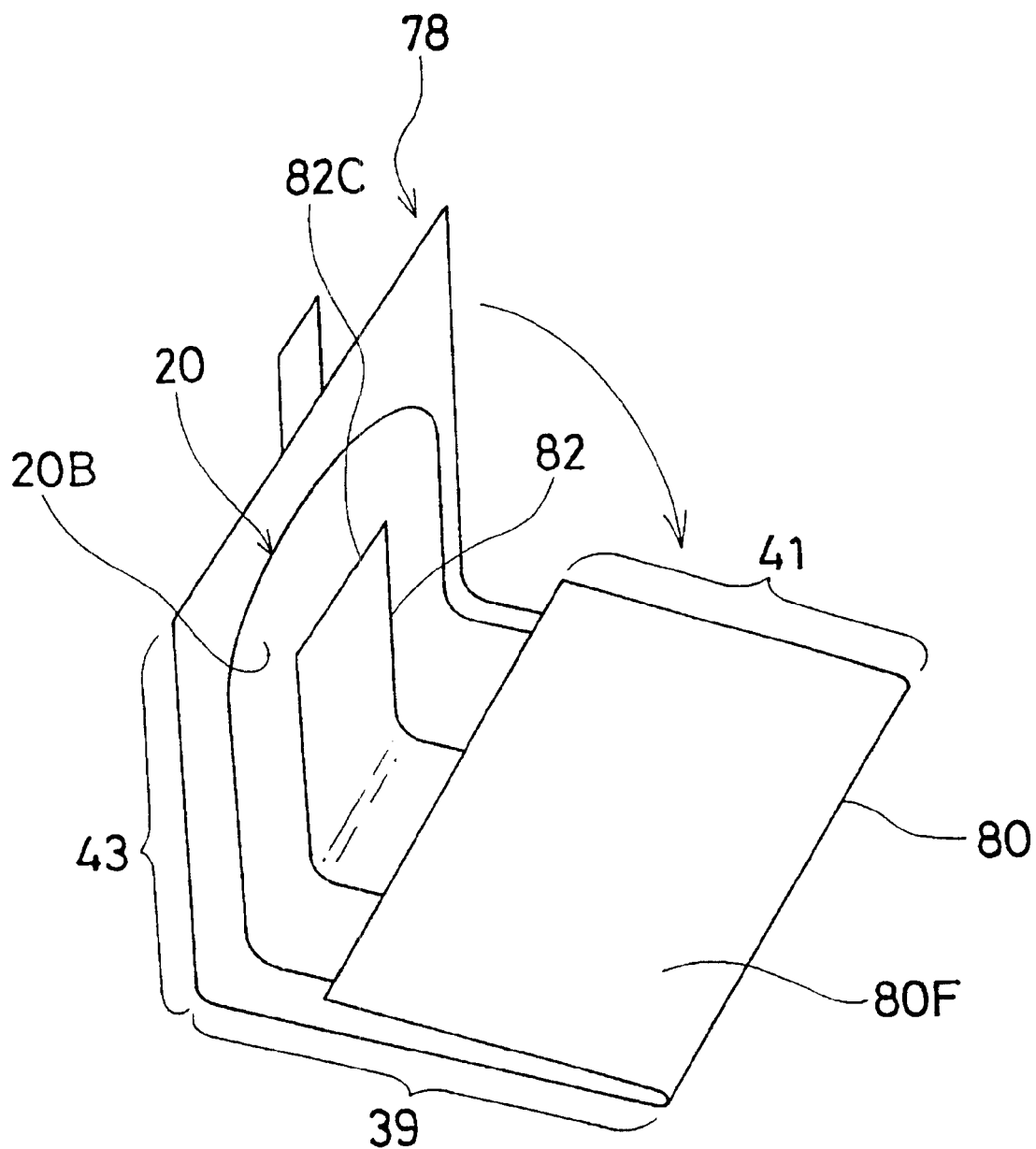
FIG. 8 is a third schematical perspective view showing a packaging process of the sanitary napkin by the wrapper.
Figure 9:
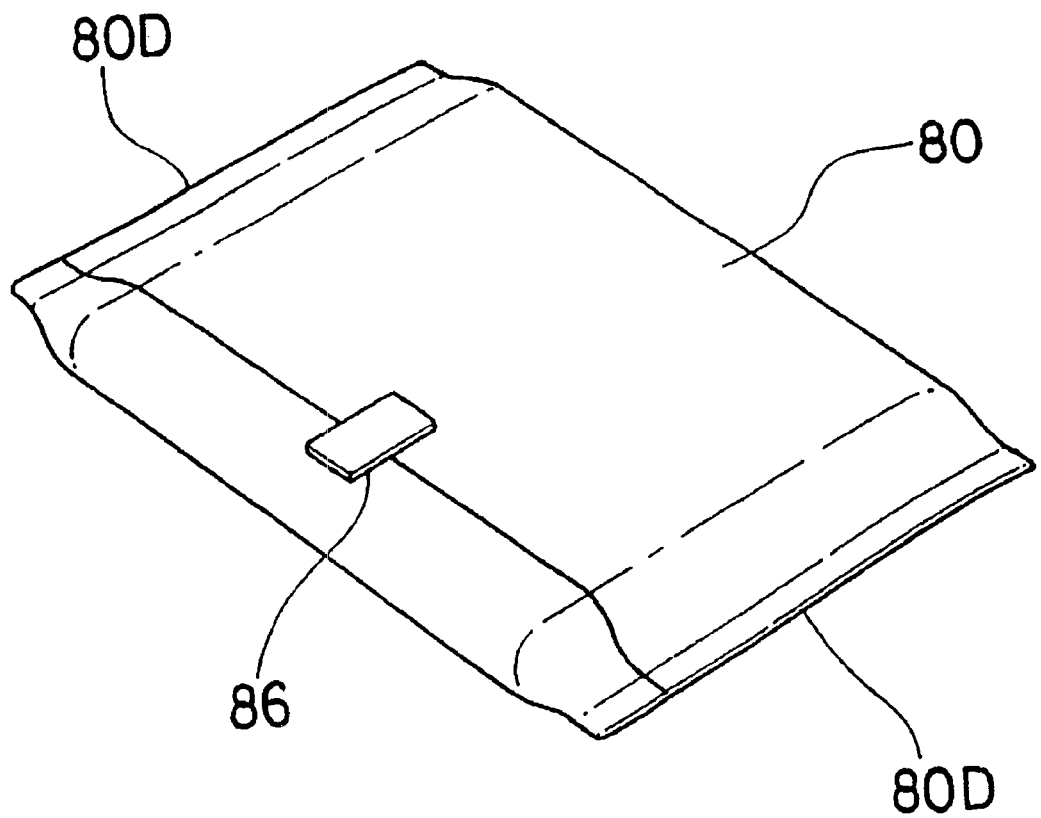
FIG. 9 is a perspective view of an embodiment of individually packaged absorbent article of the present invention assembled by utilizing the processes shown in FIGS. 6–8.

FIGS. 6–8 show one example of a process for packaging the sanitary napkin 20 in the wrapper 78. In this embodiment, the flap adhesive cover 81 is a separate flap adhesive cover sheet and the main adhesive cover 82 is a separate single sheet. Prior to packaging the sanitary napkin 20 in the wrapper 78, the first flaps 24 are folded onto the topsheet 38 (i.e., body surface 20A). Folding the flaps 24 in the configuration shown in FIG. 6 exposes the patches of adhesive 76 disposed on the garment surface 20B of flaps 24 and causes the flaps 24 to cover at least a portion of the topsheet 38. The folded left and right flaps 24 are connected to each other by the flap adhesive cover 81. The flap adhesive cover 81 covers the first flap adhesives 76 (not shown in FIGS. 6–8) and maintains the first flaps 24 in position folded over the topsheet 38. The adhesive layer 90 is provided on the opposite side 81B of the flap adhesive cover 81. As shown in FIGS. 6 and 7, the sanitary napkin 20 is placed on top of the main wrapper sheet 80 (i.e., the inner surface 80E) such that the opposite side 81B of the flap adhesive cover 81 faces the inner surface 80E of the main wrapper sheet 80. Thereby the flap adhesive cover 81 is joined to the main wrapper sheet 80 by the adhesive layer 90. The body surface 20A faces the inner surface 80E of the main wrapper sheet 80. Disposing the body surface 20A of the sanitary napkin 20 facing the main wrapper sheet 80 can be considered to provide protection to prevent the topsheet 38 from becoming soiled prior to use. Alternatively, the flap adhesive cover 81 may be joined to the inner surface 80E of the main wrapper-sheet 80 before the flap adhesive cover 81 is releasably affixed to the first flap adhesives 76. In this case, the, sanitary napkin 20 is placed on top of the main wrapper sheet 80 such that the first flap adhesives 76 lies over the flap adhesive cover 81 on the main wrapper sheet 80. The main body adhesive 74 on the garment surface 20B may be covered by the main adhesive cover 82 as shown in FIG. 7 if the main body adhesive 74 is provided. After disposing the sanitary napkin 20 on the main wrapper sheet 80 as described above, the sanitary napkin 20 will then preferably be folded as a unit, together with the wrapper 78 including the main wrapper sheet 80, the flap adhesive cover 81, and the main adhesive cover 82, into three regions that are defined by the fold axes F1 and F2. The fold axes F1 and F2 will divide both the sanitary napkin 20 and the wrapper 78 into three regions including the first region 39, the second region 41 and the third region 43. As shown in FIG. 7, the central region (the first region) 39 lies between preferred fold axes F1 and F2. The second and third regions 41 and 43 lie longitudinally outboard of the fold axes F1 and F2. As described above, the main body portion 22 is also separated at the fold axes F1 and F2 into three sections including the first section 36, the second section 34, and the third section 32. Each section 36, 34 and 32 generally extends in each region 39, 41 and 43 respectively (refer to FIG. 1 as well). As shown in FIG. 7, the sanitary napkin 20 and the wrapper 78 of the second region 41 is folded as a unit toward the sanitary napkin 20 of the first region 39 such that the garment surface 20B of the sanitary napkin 20 is oriented inwardly with respect to the folded unit and the main wrapper sheet 80 is oriented outwardly with respect to the folded unit (refer to FIG. 8 as well). Then, the sanitary napkin 20 and the wrapper 78 of the third region 43 is folded onto the wrapper 78 (i.e., the main wrapper sheet 80) of the second region 41 such that the garment surface 20B of the third region 43 faces the outer surface 80F of the main wrapper sheet 80. The body surface 20A of the sanitary napkin 20 is covered by the main wrapper sheet 80 in the folded configuration. In addition, the garment surface 20B is oriented inwardly with respect to the folded unit of the sanitary napkin 20 and the wrapper 78. Preferably, in the folded configuration, the sanitary napkin 20 is fully wrapped by the main wrapper sheet 80 and is not exposed outside the main wrapper sheet 80 (i.e., neither the body surface 20A and the garment surface 20B are exposed outside the main wrapper sheet 80). Alternatively, the sanitary napkin 20 may be folded together with the wrapper 78 into two regions that are divided by one fold axis. In such a case, the sanitary napkin 20 and the wrapper 78 are folded about the axis such that a part of the sanitary napkin 20 in one region faces a part of the sanitary napkin 20 in the other region. In this configuration, the garment surface of the sanitary napkin 20 is oriented inwardly to the folded unit of the sanitary napkin and the wrapper. Preferably, to complete the individual packaging of the sanitary napkin 20 in the wrapper 78, each longitudinal side portion 80D of the main wrapper sheet 80 is then frangibly sealed as shown in FIG. 9 after the sanitary napkin 20 and the wrapper 78 are in the folded configuration. The frangible sealing of the longitudinal side portions 80D of the main wrapper sheet 80 can be accomplished by any suitable sealing technique. By way of example only, the longitudinal side portions 80D may be heat sealed, glued, or ultrasonically bonded. The entire sanitary napkin 20 is thereby protected until the main wrapper sheet 80 is opened. Suitable methods for frangibly sealing the longitudinal side portions are described in, e.g., U.S. Pat. No. 4,556,146 issued to Swanson. FIG. 9 depicts the package for the sanitary napkin formed by folding the wrapper 78 and sanitary napkin 20 in one preferred configuration for shipment, sale, and convenient carrying by the wearer.

Figure 10:
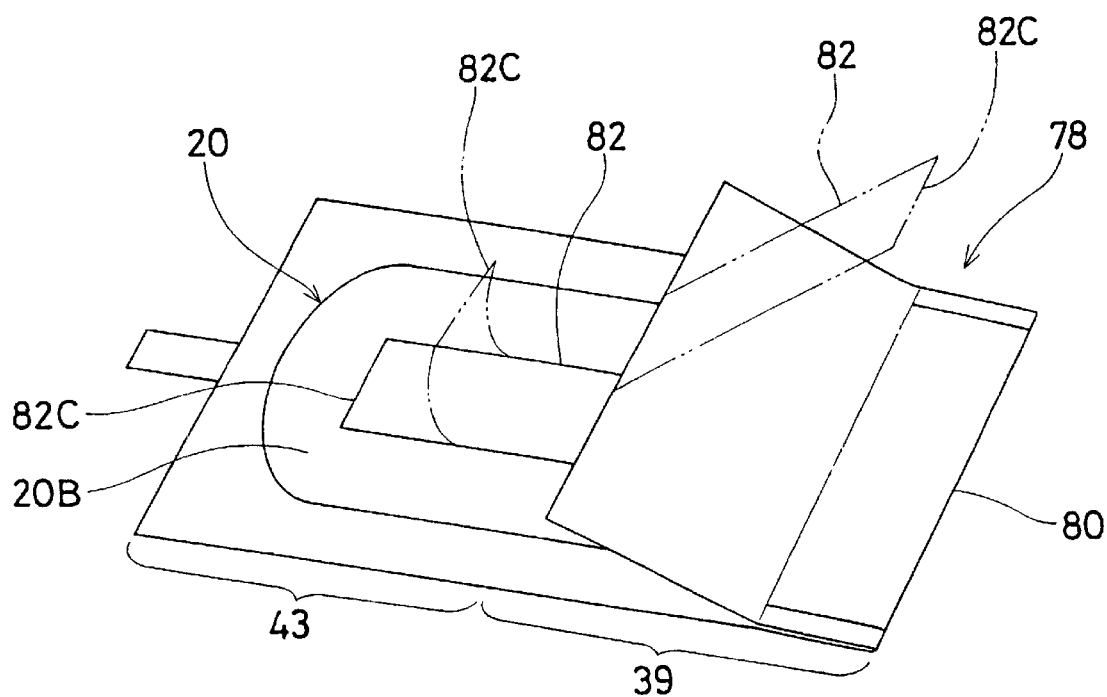
FIG. 10 is a schematical perspective view showing an opening process of the individually packaged sanitary napkin assembled by utilizing the processes shown in FIGS. 6–8.

The wearer will ordinarily carry the individually packaged sanitary napkin in the form depicted in FIG. 9. The individually packaged sanitary napkin may be opened by peeling the package fastener 86 from the wrapper 78 and breaking the frangible seals along the longitudinal side portions 80D of the main wrapper sheet 80 such that the sanitary napkin 20 of the third region 43 (not shown in FIG. 9) is opened from the main wrapper sheet 80 of the second region 41. This gives the wearer access to the first end portion 82C of the main adhesive cover 82 in the third region 43. FIG. 8 may be referred to for the configuration of the opened sanitary napkin (although FIG. 8 shows a perspective view of one step of packaging process for the sanitary napkin, the configuration of the opened sanitary napkin is similar to the configuration shown in FIG. 8.). The wearer may then take hold of the first end portion 82C and pull the first end portion 82C as shown in FIG. 10. While the main adhesive cover 82 is removed from the garment surface 20B of the sanitary napkin 20, the main adhesive cover 82 pulls the sanitary napkin 20 and the wrapper 78 of the second region 41 (not shown in FIG. 10). Thereby the sanitary napkin 20 and the wrapper 78 of the second region 41 is automatically opened from the sanitary napkin 20 of the first region 39 by a motion of pulling the main adhesive cover 82. Therefore, removal of the main adhesive cover 82 from the sanitary napkin 20 and open of the second region 41 from the first region 39 are achieved in a single motion. Upon removal of the main adhesive cover 82, the main body adhesive 74 is exposed so that it will be able to attach to the crotch region of the undergarment while the body surface 20A of the sanitary napkin 20 is still covered by the main wrapper sheet 80. Alternatively, after the third region 43 is opened from the second region 41, the wearer may open the second region 41 from the first region 39. (Refer to FIG. 7. Although FIG. 7 shows a perspective view of one step of packaging process for the sanitary napkin, the configuration of the opened sanitary napkin is similar to the configuration shown in FIG. 7.). Then the wearer may remove the main adhesive cover 82 from the sanitary napkin 20.

Figure 11:
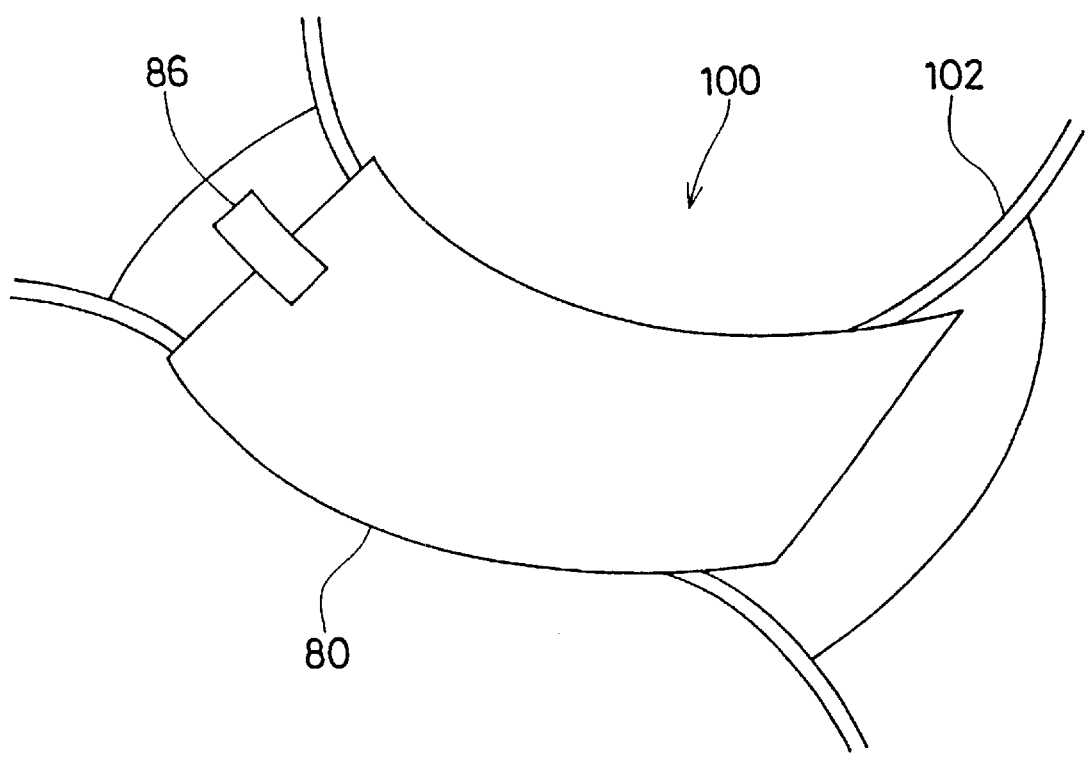
FIG. 11 is a first schematical perspective view showing an applying process of the sanitary napkin to the undergarment assembled by utilizing the processes shown in FIGS. 6–8.

As shown in FIG. 11, the sanitary napkin 20, whose body surface 20A is covered by the main wrapper sheet 80, is placed on the crotch portion 100 of the undergarment 102 such that the main adhesive 74 (now exposed) faces the inside of the crotch region 100. This can be done without touching the body surface 20A (which will subsequently directly touch the wearer's body during use) because the body surface 20A is still covered by the main wrapper sheet 80. In addition, the first flap adhesive 76 does not inadvertently stick to the hands of the wearer or a portion of the sanitary napkin 20 because the first flap adhesive 76 is covered by the main wrapper sheet 80. During application process of the sanitary napkin 20 to the undergarment 102, the main wrapper sheet 80 does not easily detach from the sanitary napkin 20 because the main wrapper sheet 80 and the sanitary napkin 20 are affixed to each other by means of the first flap adhesive 76. Although the main wrapper sheet 80 is releasably affixed to the sanitary napkin 20, it can be controlled such that the main wrapper sheet 80 does not easily detach from the sanitary napkin 20 during application process of the sanitary napkin 20 to the undergarment The configuration (how large the first flap fasteners are) and/or adhering strength of the first flap adhesive 76 may be independently chosen to control it. Adjustment of the configuration (e.g., bigger area of adhesive) and/or adhering strength (e.g., higher average adhering strength of adhesive) has no impact to wearer's skin comfortableness during the use of the sanitary napkin 20. As the configuration of the first flap adhesive 76 becomes bigger and/or adhering strength becomes higher, the main wrapper sheet 80 becomes tends not to detach from the absorbent article. In addition, because the first flap adhesive 76 is utilized to releasably affix the main wrapper sheet 80 to the sanitary napkin 20, no additional means to affix the main wrapper sheet 80 and the sanitary napkin 20, such as adhesives provided on the topsheet which may cause skin problem or cause the wearer to feel stickiness, is necessary. Because the body surface 20A (not shown in FIG. 11) is covered by the main wrapper sheet 80, the body surface 20A is protected from contamination during the application process of the sanitary napkin to the undergarment. Therefore, the wearer may push the side of the main wrapper sheet 80 toward the undergarment 102 to secure the main adhesive 74 to the crotch portion 100.

Figure 12:
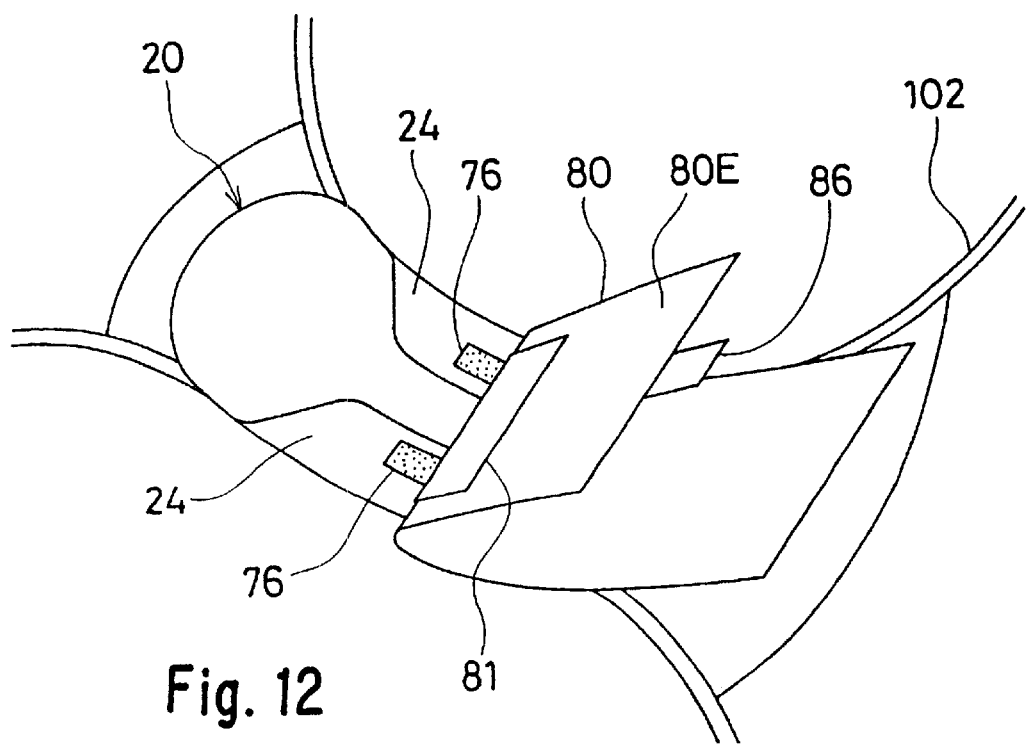
FIG. 12 is a second schematical perspective view showing an applying process of the sanitary napkin to the undergarment assembled by utilizing the processes shown in FIGS. 6–8.
Figure 13:
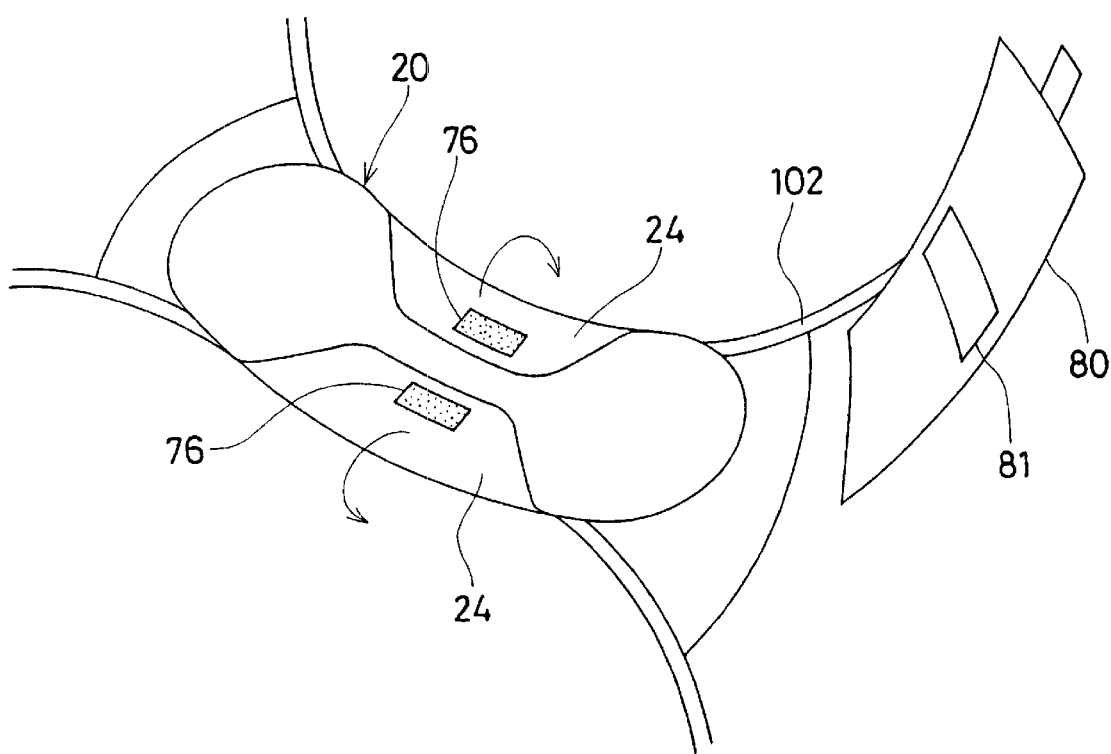
FIG. 13 is a third schematical perspective view showing applying process of the sanitary napkin to the undergarment assembled by utilizing the processes shown in FIGS. 6–8.

Then the wearer pulls the package fastener 86 to remove the main wrapper sheet 80 from the sanitary napkin 20 which is secured to the crotch portion 100 of the undergarment 102. As shown in FIG. 12, as the main wrapper sheet 80 is removed, the flap adhesive cover 81 which is joined to the inner surface 80E of the main wrapper sheet 80 is removed from the first flap adhesive 76. The wearer further pulls the main wrapper sheet 80 to remove the main wrapper sheet 80 from the sanitary napkin 20 as shown in FIG. 13. After the completion of removal, the wearer flips over the first flaps 24 toward the outside surface of the undergarment 102. Once the sanitary napkin is removed from the wrapper 78 and installed in the wearer's undergarment, the wearer may fold the wrapper 78, secure the wrapper 78 in its folded orientation by reattaching resealable package fastener 86 to wrapper 78. The wearer may then store the folded wrapper 78 for rewrapping and disposing of the used sanitary napkin. The wearer need not worry about collecting and disposing of loose flap adhesive cover 81 since the flap adhesive cover 81 is joined to the main wrapper sheet 80. Therefore, the present invention provides the wearer with a clean sanitary napkin 20 which is easily installed while keeping the body surface hygienic and without extra pieces of waste which must be collected. FIGS. 14–20 show an alternative embodiment of the wrapper 78. The wrapper 78 includes a main wrapper sheet 80, a flap adhesive cover 81 (not shown in FIGS. 14–18), and a main adhesive cover 82. In this embodiment, both the flap adhesive cover 81 and the main adhesive cover 82 are joined to the main wrapper sheet 80. In this alternative embodiment, the sanitary napkin 20 is placed on the main wrapper sheet 80 accordance with the same process as explained referring to FIG. 6 such that the body surface 20A of the sanitary napkin 20 faces the inner surface 80E of the main wrapper sheet 80. In this embodiment, the adhesive layer 91 is provided on the opposite side 82B of the main adhesive cover 82 proximate to the first end portion 82C of the main adhesive cover 82. The sanitary napkin 20 and the wrapper 78 of the second region 41 is folded toward the sanitary napkin 20 of the first region 39, then the sanitary napkin 20 and the wrapper 78 of the third region 43 is folded onto the main wrapper sheet 80 of the second region 41 as shown in FIG. 15. The first end portion 82C of the main adhesive cover 82 of the third region 43 joins to the outer surface 80F of the main wrapper sheet 80 proximate to the second end portion 80B of the second region 41 (not shown in FIG. 15) by the adhesive layer 91. After that, the individual packaging of the sanitary napkin 20 in the wrapper 78 is completed by the same process as described above. The completed individual packaging of the sanitary napkin 20 may be the same configuration as shown in FIG. 9.

Figure 14:
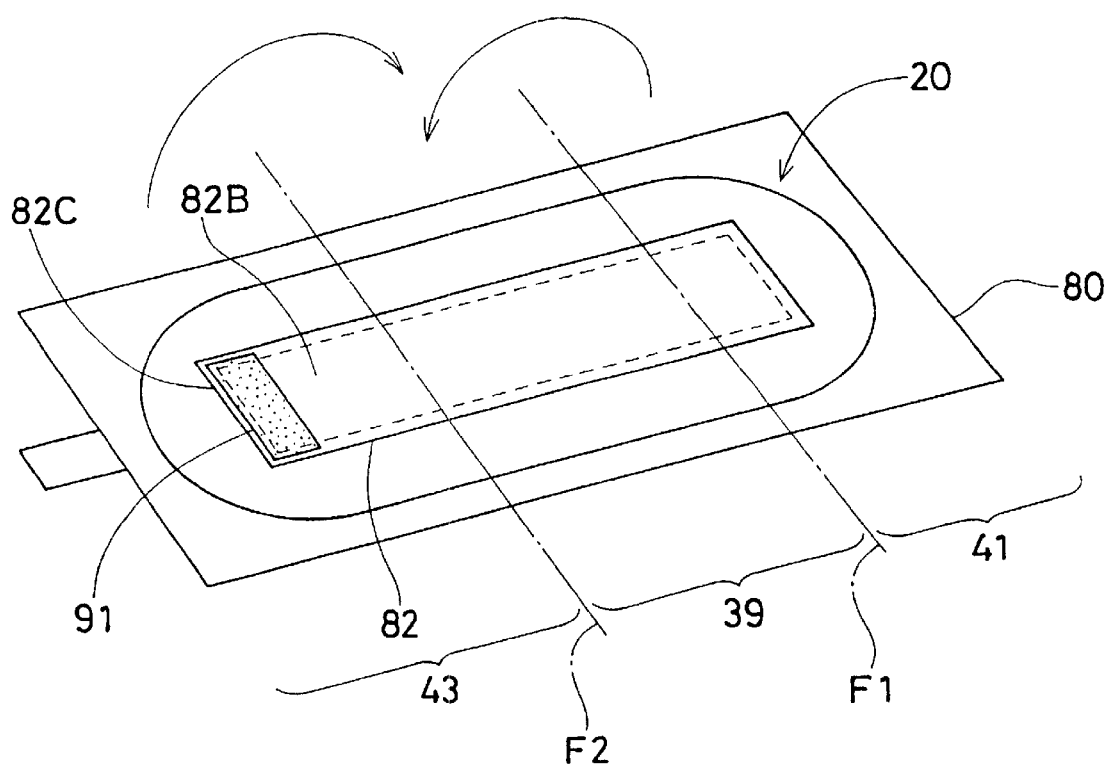
FIG. 14 is a first schematical perspective view of an alternative embodiment showing a packaging process of the sanitary napkin by, the wrapper.
Figure 15:
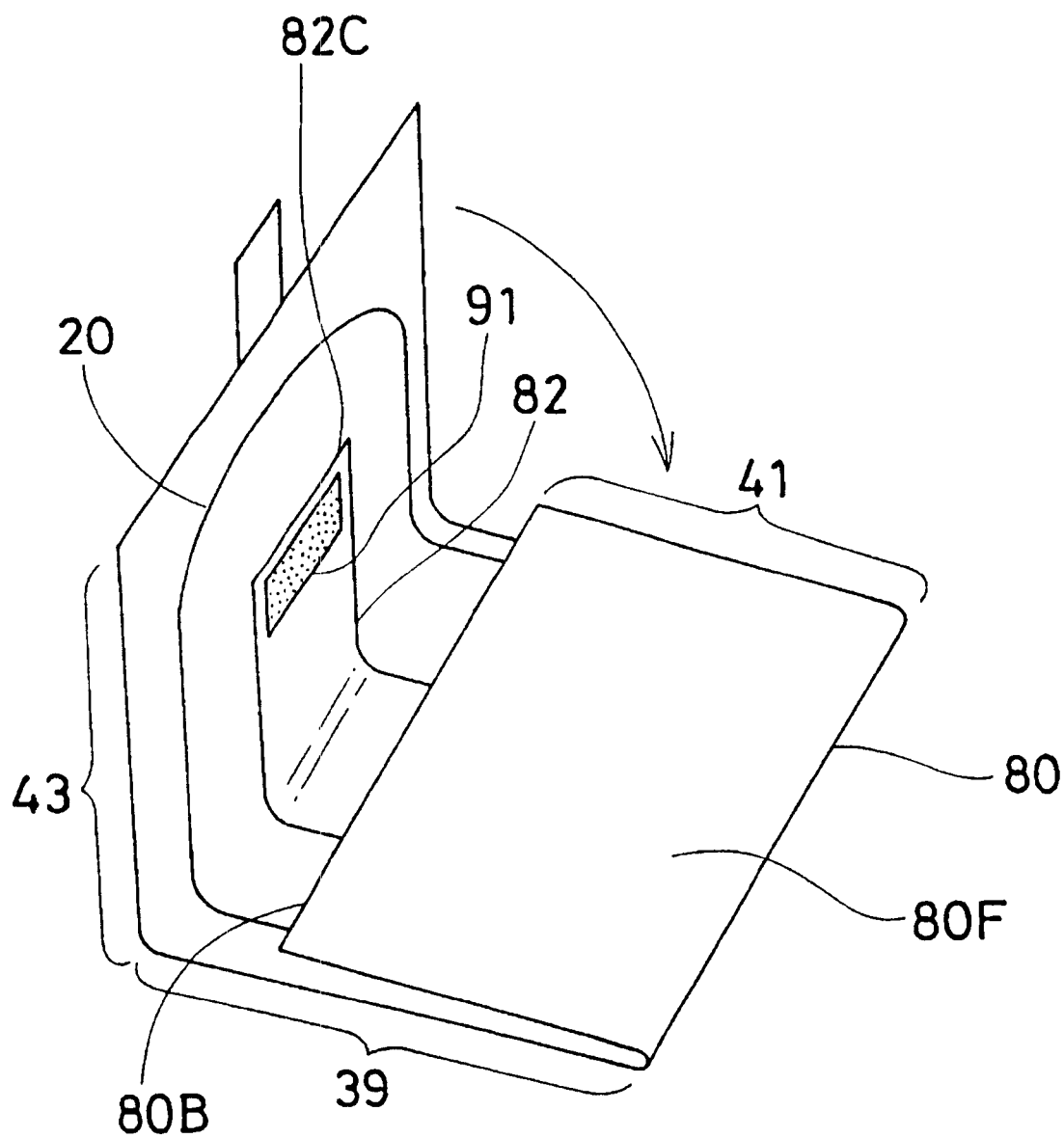
FIG. 15 is a second schematical perspective view of an alternative embodiment showing a packaging process of the sanitary napkin by the wrapper.
Figure 16:
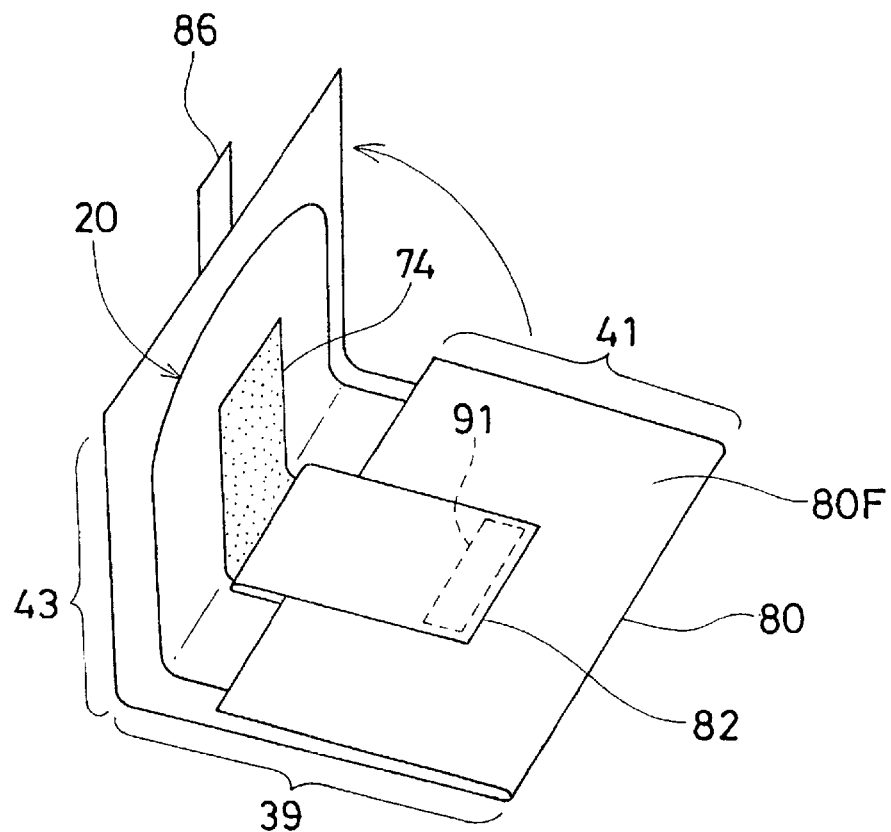
FIG. 16 is a first schematical perspective view showing an opening process of the individually packaged sanitary napkin assembled by utilizing the processes shown in FIGS. 14–15.
Figure 17:
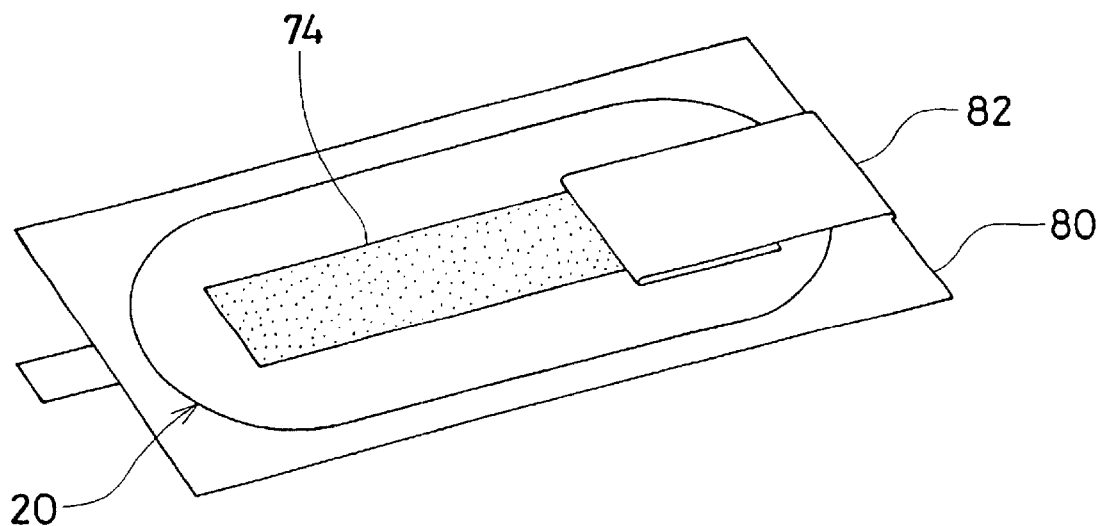
FIG. 17 is a second schematical perspective view showing an opening process of the individually packaged sanitary napkin assembled by utilizing the processes shown in FIGS. 14–15.

When the wearer opens the individually packaged sanitary napkin assembled by utilizing the processes shown in FIGS. 14–15 by peeling the package fastener 86 from the wrapper 78 (i.e., the third region 43 is opened from the second region 41), the first end portion 82C of the main adhesive cover 82 remains on the outer surface 80F of the main wrapper sheet 80 because of the adhesive layer 91 as shown in FIG. 16. Thereby, a part of the main body adhesive 74 located in the third region 43 is, automatically exposed as the third region 43 is opened from the second region 41. Then the second region 41 is opened from the first region 39 in order to further expose the main body adhesive 74 as shown in FIG. 17.

Figure 18:
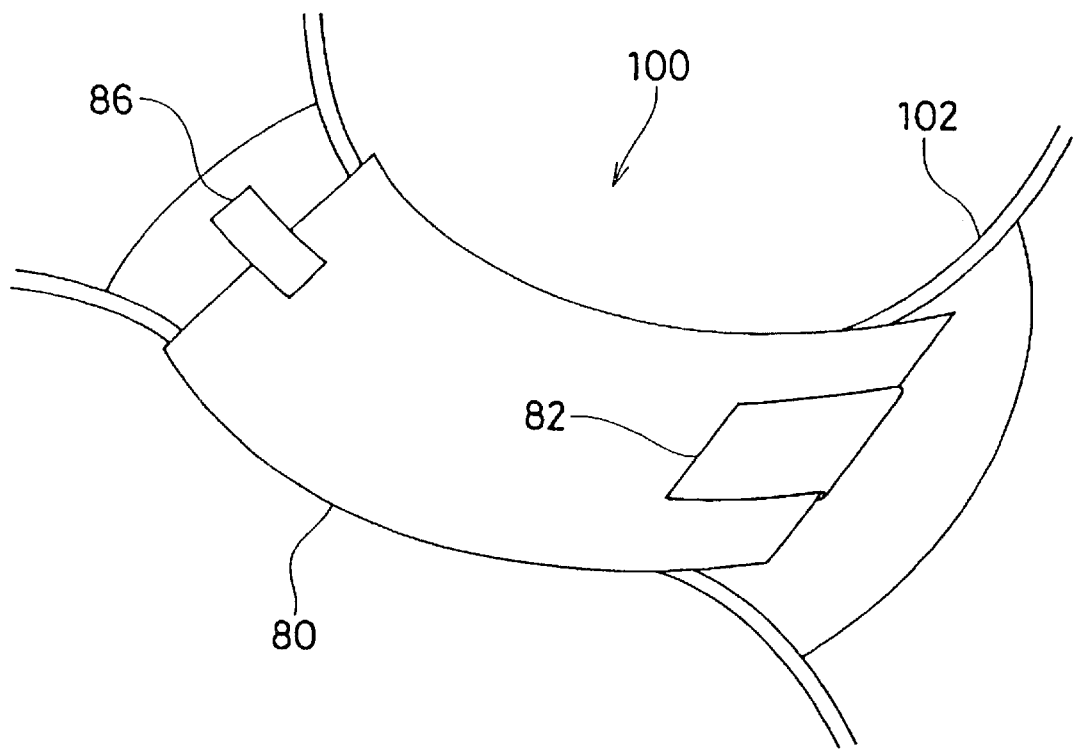
FIG. 18 is a first schematical perspective view showing an applying process of the sanitary napkin to the undergarment assembled by utilizing the processes shown in FIGS. 14–15.
Figure 19:
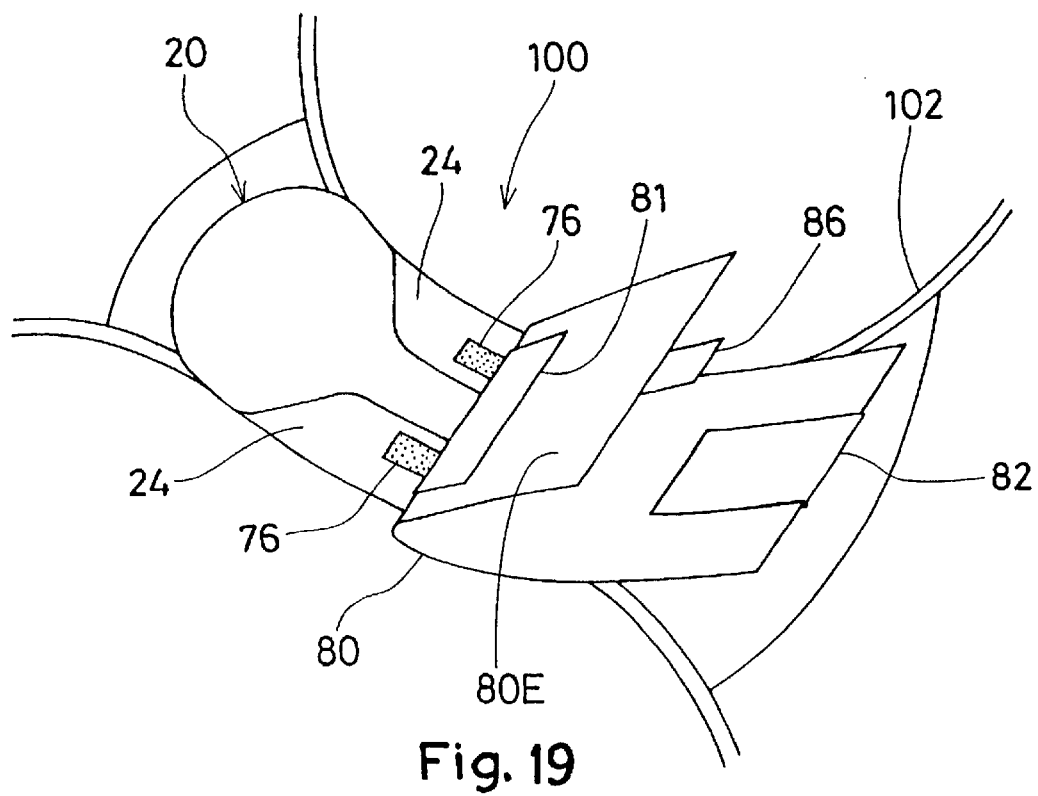
FIG. 19 is a second schematical perspective view showing an applying process of the sanitary napkin to the undergarment assembled by utilizing the processes shown in FIGS. 14–15.
Figure 20:
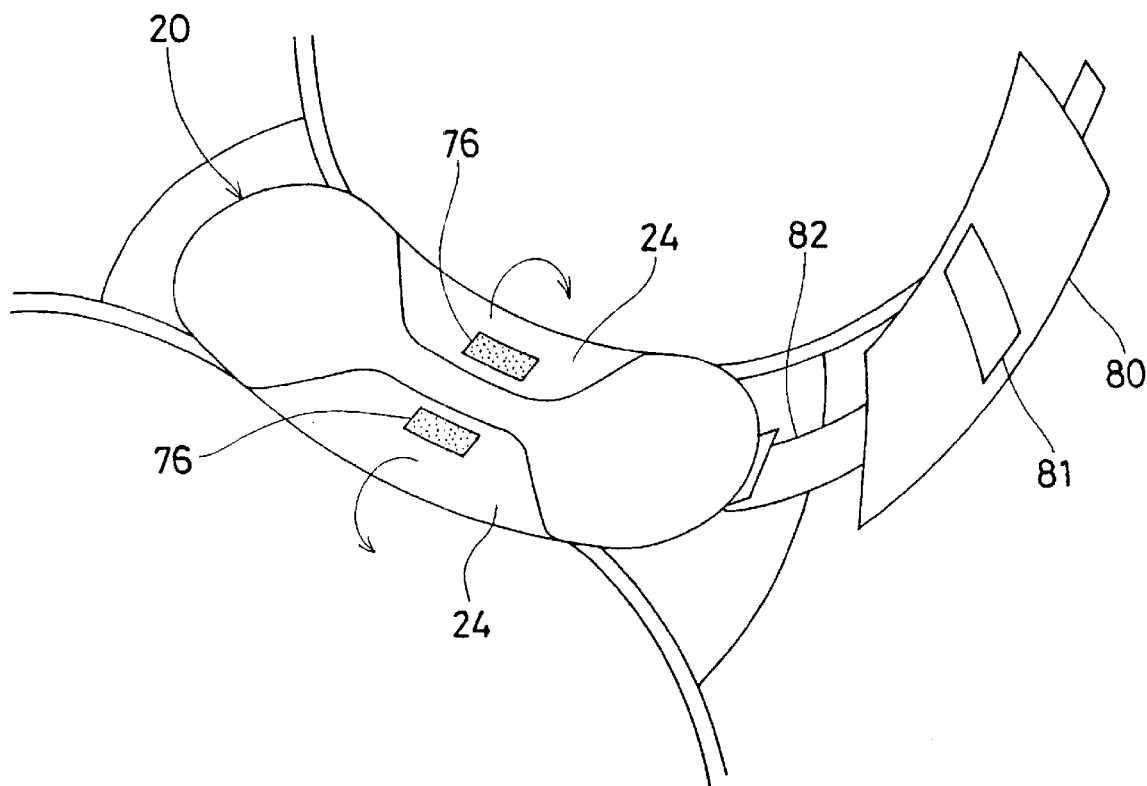
FIG. 20 is a third schematical perspective view showing an applying process of the sanitary napkin to the undergarment assembled by utilizing the processes shown in FIGS. 14–15.
Figure 21:
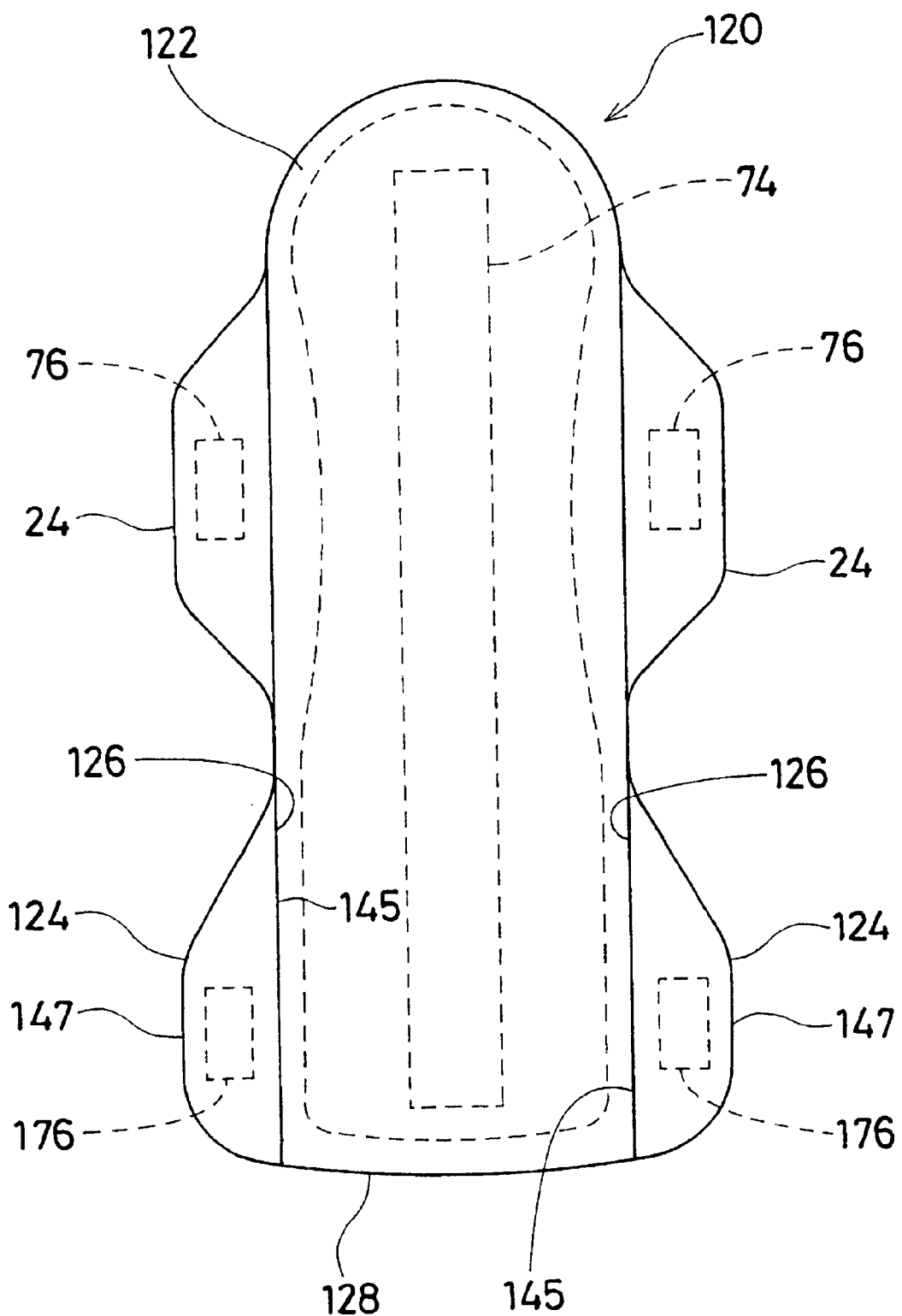
FIG. 21 is a top plan view of an alternative embodiment of a sanitary napkin of the resent invention with the flaps outstretched.
Figure 22:
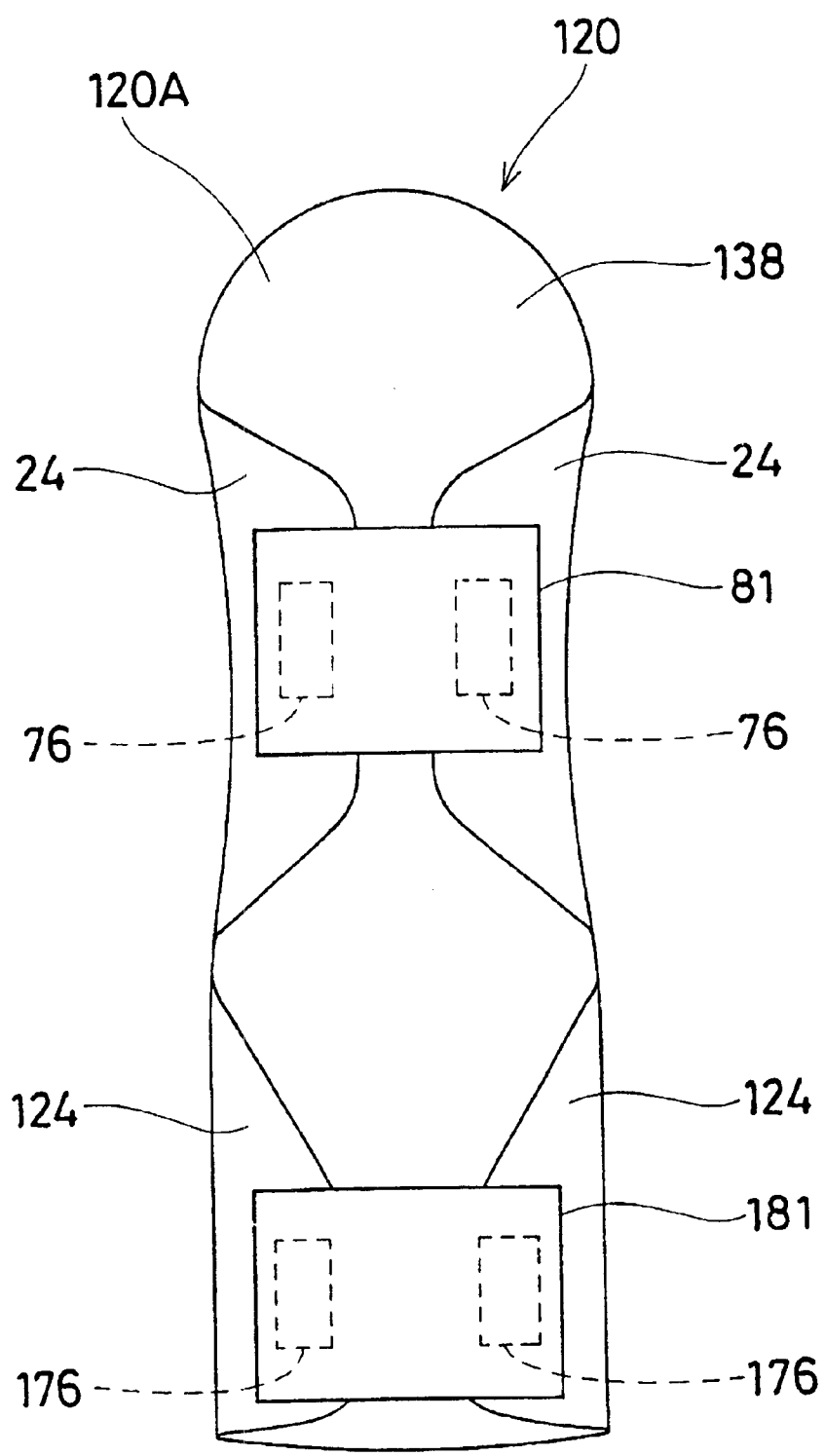
FIG. 22 is a top plan view of the sanitary napkin shown in FIG. 21 with the flaps folded over the topsheet and covered by the flap fastener cover.
Figure 23:
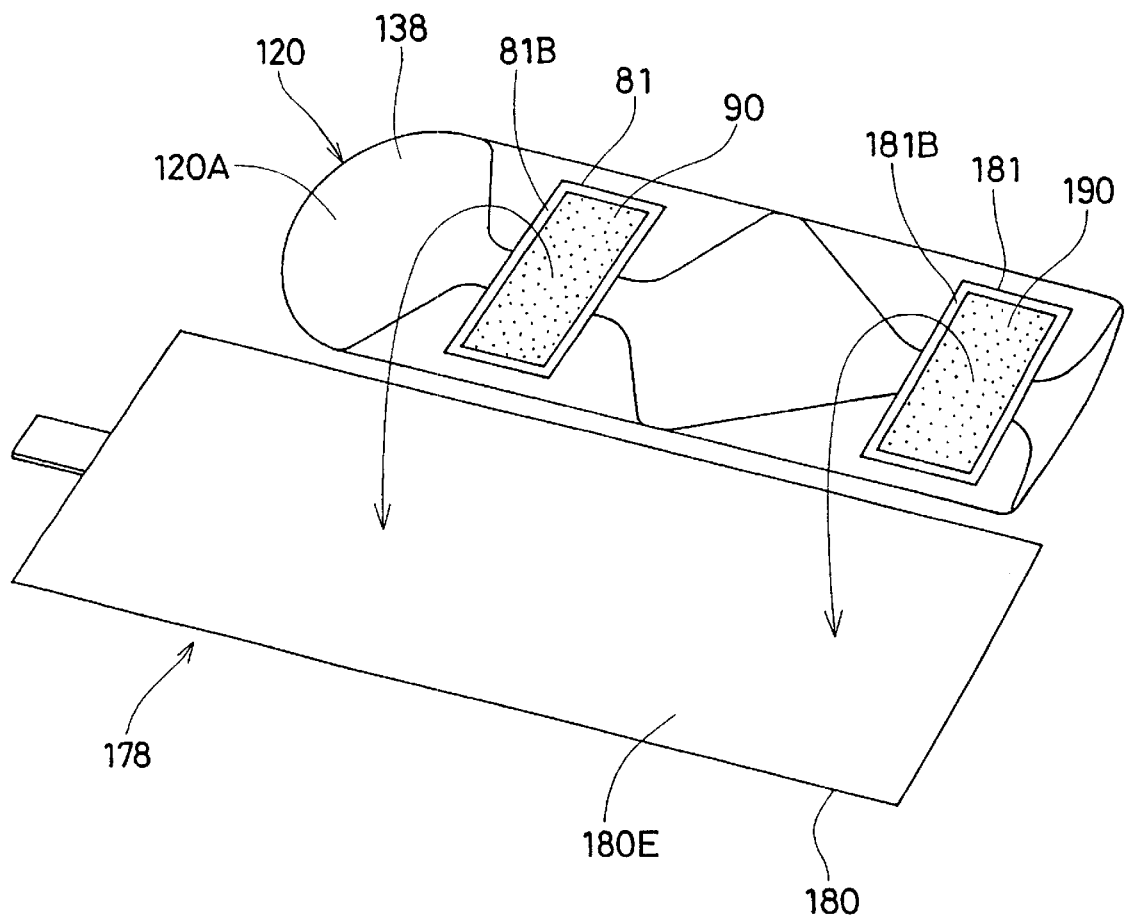
FIG. 23 is a schematical perspective view showing a packaging process for the sanitary napkin shown in FIG. 21 by the wrapper.

After that, as shown in FIG. 18, the sanitary napkin 20 whose body surface 20A is covered by the main wrapper sheet 80 is placed on the crotch portion 100 of the undergarment 102 such that the main adhesive 74 (now exposed) faces and secures to the inside of the crotch region 100. The wearer pulls the package fastener 86 to remove the main wrapper sheet 80 from the sanitary napkin 20 which is secured to the crotch portion 100 of the undergarment 102. As shown in FIG. 19, as the main wrapper sheet 80 is removed, the flap adhesive cover 81 which is joined to the inner surface 80E of the main wrapper sheet 80 is also removed from the first flap adhesive 76. The wearer further pulls the main wrapper sheet 80 to remove the main wrapper sheet 80 from the sanitary napkin 20 as shown in FIG. 20. As the main wrapper sheet 80 is further pulled, the main adhesive cover 82 is also pulled and removed in a single motion together with the main wrapper sheet 80 because the main adhesive cover 82 is joined to the main wrapper sheet 80. In addition, because the first end portion 82C of the main adhesive cover 82 of the third region 43 (rather than the second end portion 82D of the second region 41) is joined to the outer surface 80F of the main wrapper sheet 80 proximate to the second end portion 80B of the second region 41, the wearer is able to peel the main adhesive cover 82 together with the main wrapper sheet 80 from the main body adhesive 74 without feeling shear force therebetween. Thus, after placing the sanitary napkin 20 with the main wrapper sheet 80 against the crotch region 100 (FIG. 16), removal of the main wrapper sheet 80 and the main adhesive cover 82 can be done in a single motion of pulling a part of main wrapper sheet 80. After the completion of removal, the wearer flips over the first flap 24 toward the outside surface of the undergarment. FIGS. 21–23 show an alternative embodiment of the sanitary napkin and the wrapper 178. The sanitary napkin 120 shown in FIG. 21 has another additional pair of flaps 124 (second flaps). The second flaps 124 extend laterally outward beyond the longitudinal side edges 126 of the main body portion 122 from their proximal edges 145 to their distal edges (or "free ends") 147. The second flaps 124 are positioned proximate to one end edge 128 of the main body portion 122 and apart from the first flaps 24 in the longitudinal direction of the main body portion 122. The second flaps 124 preferably each have second fasteners thereon, such as a pressure sensitive adhesive fastener 176, for releasably affixing the second flaps 124 of the sanitary napkin 120 in a configuration staying widespread in a back region of the inside of a wearer's undergarment. The second flap adhesives 176 are used to assist in maintaining the second flaps 124 in position after they are rendered widespread in a back region of the inside of the panty. The wrapper 178 includes a main wrapper sheet 180, a first flap adhesive cover 81, a second flap adhesive cover 181, and a main adhesive cover (not shown in FIGS. 22 and 23) as shown in FIGS. 22 and 23. The second flap adhesive cover 181 may have the same structure and/or shape as the first adhesive cover 81. The second flap fastener cover 181 covers and protects the second flap adhesives 176, and maintains the second flaps 124 in position folded over the topsheet 138 (i.e., body surface 120A) for packaging as shown in FIG. 22.

In one embodiment of a packaging process for the sanitary napkin 120 in the wrapper 178, the first and second flaps 24 and 124 are folded onto the topsheet 138 (i.e., body surface 120A) to expose the patches of first and second adhesives 76 and 176. As shown in FIG. 23, the first and second flap adhesive covers 81 and 181 are placed to cover the first and second flap adhesives 76 and 176 and maintain the first and second flaps 24 and 124 in position folded over the topsheet 138. The second adhesive layer 190 is provided on the opposite side 181B of the second flap adhesive cover 181. The first adhesive layer 90 is also provided on the opposite side 81 B of the first flap adhesive cover 81 as explained above. The sanitary napkin 120 is placed on top of the main wrapper sheet 180 (i.e., the inner surface 180E) such that the first and second flap adhesive covers 81 and 181 are joined to the main wrapper sheet 80 by the first and second adhesive layers 90 and 190. The body surface 120A is then protected by the main wrapper sheet 180 to prevent the topsheet 138 from becoming soiled prior to use. The main body adhesive 74 may be provided and covered by the main adhesive cover. The main adhesive cover may or may not be joined to the main wrapper sheet 181. Subsequent steps to complete packaging of the sanitary napkin 120 may be the same as those steps previously discussed herein.

In this embodiment, the same benefit as explained above can be obtained. Namely, the wearer can put the sanitary napkin 120 on the crotch portion of the undergarment without touching the body surface 120A. During application process of the sanitary napkin 120 to the undergarment, the main wrapper sheet 180 does not easily detach from the sanitary napkin 120 because the main wrapper sheet 180 and the sanitary napkin 20 are affixed each other by means of the first flap adhesive 76. In addition, no additional means to affix the main wrapper sheet 180 and the sanitary napkin 120 such as adhesives provided on the topsheet which may cause skin problem or cause the wearer to feel stickiness, is necessary. The wearer may also push the side of the main wrapper sheet 180 toward the undergarment 102 to secure the main adhesive 74 to the crotch portion because the body surface 120A is covered by the main wrapper sheet 180. After the sanitary napkin is removed from the wrapper 178 and installed in the wearer's panties, the wearer also need not worry about collecting and disposing of loose flap adhesive covers 81 and 181.

In the embodiment shown in FIGS. 21–23, the first flap adhesive cover 81 and the second flap adhesive cover may be formed by a single element such as a single paper which can cover both the first flap adhesive cover 76 and the second flap adhesive cover 176.

It is to be recognized that the foregoing detailed description of the preferred embodiment of the present invention is given merely by way of illustration, and that numerous modifications and variations may become apparent to those skilled in the art without departing from the spirit and scope of the invention. Therefore, the scope of the present invention is to be determined by reference to the appended claims.

What is claimed is:

1. An individually packaged absorbent article comprising:
   (a) an absorbent article extending in a longitudinal direction and including a main body portion having a pair of longitudinal side edges, a pair of end edges, a garment surface, and a body surface, and the absorbent article including a pair of flaps joined to the main body portion and extending laterally outward beyond the longitudinal side edges of the main body portion, wherein the garment surface of each of the flaps has a flap fastener, and the flaps are folded over the body surface of the main body portion to expose the flap fasteners,
   (b) a wrapper for the absorbent article, the wrapper having a main wrapper sheet, wherein
   (c) the body surface of the main body portion is disposed to face the main wrapper sheet, and the flap fastener of the flap is releasably affixed to the main wrapper sheet, and
   (d) the main body portion and the wrapper are folded as a unit at least about one transverse axis such that the garment surface is oriented inwardly with respect to the folded unit.

2. The absorbent article of claim 1 wherein the wrapper includes a flap fastener cover provided on the main wrapper sheet, wherein the flap fastener is releasably affixed to the flap fastener cover.

3. The absorbent article of claim 2 wherein the flap fastener is an adhesive and the flap fastener cover is formed by a thin sheet-like element provided with a nonstick surface, wherein the flap fastener is releasably affixed to the nonstick surface of the flap fastener cover.

4. The absorbent article of claim 2 wherein the flap fastener is an adhesive and the flap fastener cover is formed by a release coating provided on the main wrapper sheet, wherein the flap fastener is releasably affixed to the release coating.

5. The absorbent article of claim 1 wherein the garment surface of the main body portion has a main fastener, and the wrapper has a main fastener cover, wherein the main fastener is releasably affixed to the main fastener cover.

6. The absorbent article of claim 5 wherein the main fastener cover is joined to the main wrapper sheet.

7. An individually packaged absorbent article comprising:
   (a) an absorbent article extending in a longitudinal direction and including a main body portion having a pair of longitudinal side edges, a pair of end edges, a garment surface, and a body surface, and the absorbent article including a pair of first flaps joined to the main body portion and extending laterally outward beyond the longitudinal side edges of the main body portion and a pair of second flaps joined to the main body portion apart from the first flaps in the longitudinal direction and extending laterally outward beyond the longitudinal side edges of the main body portion, wherein the garment surface of each of the first and second flaps has a first flap fastener and a second flap fastener respectively, and the first and second flaps are folded over the body surface of the main body portion to expose the first and second flap fasteners,
   (b) a wrapper for the absorbent article, the wrapper having a main wrapper sheet, wherein
   (c) the body surface of the main body portion is.disposed to face the main wrapper sheet, and the first flap fastener and the second flap fastener are releasably affixed to the main wrapper sheet, and
   (d) the main body portion and the wrapper are folded as a unit at least about one transverse axis such that the garment surface is oriented inwardly with respect to the folded unit.

8. The absorbent article of claim 7 wherein the wrapper includes a flap fastener cover provided on the main wrapper sheet, wherein the first and second flap fasteners are releasably affixed to the flap fastener cover.

9. The absorbent article of claim 8 wherein the flap fastener cover comprises a first flap fastener cover and a second flap fastener cover.

* * * * *